(12) United States Patent
Markham et al.

(10) Patent No.: US 6,326,391 B1
(45) Date of Patent: Dec. 4, 2001

(54) INHIBITORS OF MULTIDRUG TRANSPORTERS

(75) Inventors: Penelope N. Markham, Oak Park; Debbie C. Mulhearn, Wheaton; Alexander A. Neyfakh, Oak Park; David Crich, Chicago; Mohamad-Rami Jaber, Romeoville; Michael E. Johnson, Winntka, all of IL (US)

(73) Assignee: Influx, Inc., Chicago, IL (US)

( * ) Notice: Subject to any disclaimer, the term of this patent is extended or adjusted under 35 U.S.C. 154(b) by 0 days.

(21) Appl. No.: 09/454,258

(22) Filed: Dec. 2, 1999

Related U.S. Application Data

(60) Provisional application No. 60/110,841, filed on Dec. 4, 1998.

(51) Int. Cl.[7] ............... A61K 31/404; A61K 31/402; A61K 31/403; C07D 209/04
(52) U.S. Cl. ............... 514/410; 514/412; 548/452; 548/469; 548/420
(58) Field of Search ............... 514/39–410, 412; 548/452, 469, 420

(56) References Cited

U.S. PATENT DOCUMENTS

| | | | |
|---|---|---|---|
| 4,448,962 | 5/1984 | Irikura et al. | 544/362 |
| 4,499,091 | 2/1985 | Wentland et al. | 514/254 |
| 4,668,784 | 5/1987 | Mascellani et al. | 544/32 |
| 4,704,459 | 11/1987 | Todo et al. | 546/123 |
| 4,795,751 | 1/1989 | Matsumoto et al. | 514/254 |
| 5,532,239 | 7/1996 | Pruna | 514/254 |
| 5,883,074 | 3/1999 | Boggs et al. | 514/8 |
| 5,989,832 | 11/1999 | Trias et al. | 435/7.2 |

FOREIGN PATENT DOCUMENTS

| | | |
|---|---|---|
| 3142854 | 5/1983 | (DE) . |
| 206283 | 12/1986 | (EP) . |

OTHER PUBLICATIONS

Acar and Goldstein, "Trends in bacterial resistance to fluoroquinolones," *Clin. Infect. Dis.*, 24(1):67–73, 1997.

Ahmed et al., "Mutants of the *Bacillus subtilis* multidrug transporter Bmr with altered sensitivity to the antihypertensive alkaloid reserpine," *J. Biol. Chem.*, 268:11086–11089, 1993.

Ahmed et al., "A protein that activates expresssion of a multidrug efflux transporter upon binding the transporter substrates," *J. Biol. Chem.*, 269:28506–28513, 1994.

Ahmed et al., "Two highly similar multidrug transporters of *Bacillus subtilis* whose expression is differentially regulated," *J. Bacteriol.*, 177:3904–3910, 1995.

Baranova and Neyfakh, "Apparent involvement of a multidrug transporter in the fluoroquinolone resistance of *Streptococcus pneumoniae*," *Antimicrob. Agents Chemother.*, 41:1396–1398, 1997.

(List continued on next page.)

*Primary Examiner*—Alan L. Rotman
*Assistant Examiner*—Rita Desai
(74) *Attorney, Agent, or Firm*—Fulbright & Jaworski

(57) ABSTRACT

The present invention relates generally to the fields of bacteriology and mycology. More particularly, the present invention provides novel inhibitors of multidrug transport proteins that may be used in combination with existing antibacterial agent and/or antifungal agents to increase the toxic effects of the antimicrobial agents. More specifically the present invention provides methods and compositions for enhancing the antibacterial action of fluoroquinolones by administering fluoroquinolones in combination with an inhibitor of multidrug transporters and of enhancing the antifungal action of azole antifungal agents by administering an azole antifungal agent in combination with an inhibitor of multidrug transporters. Compositions comprising indole, urea, quinoline or aromatic amide based inhibitors also are disclosed.

14 Claims, 9 Drawing Sheets

OTHER PUBLICATIONS

Figure 1:
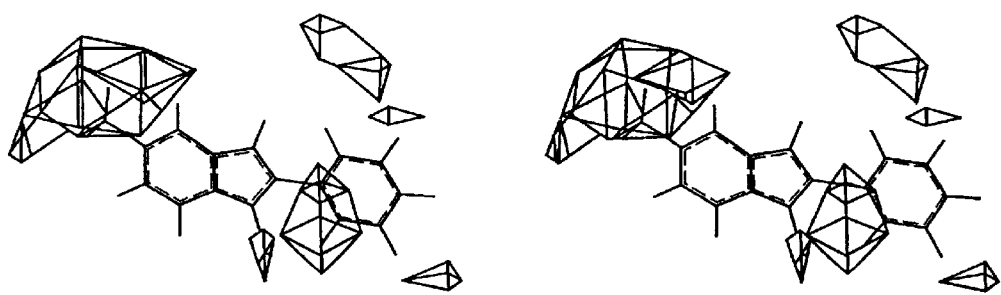

Bolhuis et al., "The Lactococcal lmrP gene encodes a proton motive force–dependent drug transporter." *J Biol Chem.* 270(44): 26092–29098, 1995.

Brenwald et al., "The effect of reserpine, an inhibitor of multidrug efflux pumps, on the in vitro susceptibilities of fluorquinolone–resistant strains of *Streptococcus pneumoniae* to norfloxacin," *Antimicrob. Agents Chemother.*, 40:458–460, 1997.

Brown, "The pyrimidines," Wiley Interscience, NY, pp 1–1509, 1994.

Cambau and Gutman, "Mechanisms of resistance to quinolones," *Drugs*, 45:15–23, 1993.

Cormican and Jones, "Emerging resistance to antimicrobial agents in gram positive bacteria," *Drugs*, 51(1):6–12, 1996.

Davis et al., "Ciprofloxacin: an updated review of its pharmacology, therapeutic efficacy and tolerability" *Drugs*, 51(6):1019–1074, 1996.

Eliopoulus and Moellering, Antimicrobial combinations, In: *Antibiotics in laboratory medicine*, (ed.) Lorian, The Williams and Wilkins Co., Baltimore, Md., pp. 330–396, 1996.

Ferrero et al., "Cloning and primary structure of *Staphylococcus aureus* DNA topoisomerase IV: a primary target of fluoroquinolones," *Mol. Microbiol.*, 13:641–653, 1994.

Kaatz and Seo, "Inducible NorA–mediated multidrug resistance in *Staphylococcus aureus*," *Antimicrob. Agents Chemother.*, 39:2650–2655, 1995.

Kaatz, et al., "Mechanisms of fluoroquinolone resistance in *Staphylococcus aureus*," *J. Infect. Dis.*, 163:1080–1086, 1990.

Korten et al., "Analysis by PCR and direct sequencing of gyrA mutations associated with fluoroquinolone resistance *Enterococcus faecalis*," *Antimicrob. Agents Chemother.*, 38:2091–2094, 1994.

Lewis, "Multidrug–resistance pumps in bacteria: variations on a theme," *Trends Biochem. Sci.*, 19:119–123, 1994.

Lynch et al., "Active efflux of antimicrobial agents in wild–type strains of *Enterococci*," *Antimicrob. Agents Chemother.*, 41:869–871, 1997.

Markham and Neyfakh, "Inhibition of the multidrug transporter NorA prevents emergence of norfloxacin resistance in *Staphylococcus aureus*," *Antimicrob. Agents Chemother.*, 40:2673–2674, 1996.

Martin et al., "A fast new approach to pharmacophore mapping and its application to dopaminergic and benzodiazepine agonists" *J. Computer–Aided Molec. Design*, 7:83–102, 1993.

Maryanoff and Reitz "The Wittig Olefination Reaction and modifications involving Phosphoryl–stabilized carbanions. Stereochemistry, mechanism and selected synthetic aspects", *Chem. Rev.* 89, 863–927, 1989.

Munoz and De La Campa, "ParC subunit of DNA topoisomerase IV of *Streptococcus pneumoniae* is a primary target of fluoroquinolones and cooperates with DNA gyrase A subunit in forming resistance phenotype," *Antimicrob. Agents Chemother.*, 40:2252–2257, 1996.

Neyfakh et al., "Efflux–mediated multidrug resistance in *Bacillus subtilis*: similarities and dissimilarities with the mammalian system," *Proc. Natl. Acad. Sci. USA*, 88:4781–4785.

Neyfakh et al., "Fluoroquinolone resistance protein NorA of *Staphylococcus aureus* is a multidrug efflux transporter," *Antimicrob. Agents Chemother.*, 37:128–129, 1993.

Nikaido, "Prevention of drug access to bacterial targets: permeability barriers and active efflux," *Science*, 264:382–388, 1994.

Ohki and Murata, "bmr3, a third multidrug transporter gene of *Bacillus subtilis*," *J. Bacteriol.*, 179:1423–1427, 1997.

Okusu et al., "AcrAB efflux pump plays a major role in the antibiotic resistance phenotype of *E. coli* multiple–antibiotic–resistance (Mar) mutants," *J. Bacteriol.*, 178:306–308, 1996.

Poole et al., "Multiple antibiotic resistance in *Pseudomonas aeruginosa*: evidence for involvement of an efflux operon," *J. Bacteriol.*, 175:7363–7372, 1993.

Stein, "Kinetics of the multidrug transporter (P–glycoprotein) and its reversal," *Physiol. Rev.*, 77:545–589, 1997.

Takiff et al., "Efflux pumps of the proton antiporter family confers low level fluoroquinolone resistance in *Mycobacterium smegmatis*," *Proc. Natl. Acad. Sci. USA*, 93:362–366, 1996.

Tankovic et al., "Contribution of mutations in gyrA and parC genes to fluoroquinolone resistance of mutants of *Streptococcus pneumoniae* obtained in vivo and in vitro," *Antimicrob. Agents Chemother.*, 40:2505–2510, 1996.

Trucksis et al., "A novel locus conferring fluoroquinolone resistance in *Staphylococcus aureus*," *J. Bacteriol.*, 173:5854–5860, 1991.

U.S. Food and Drug Administration, "New antimicrobial agents approved in 1996 and new indications for previously used agents," *Antimicrob. Agents Chemother.*, 41:878, 1997.

van Veen et al., "Multidrug resistance mediated by a bacterial homolog of the human multidrug transporter MDR1." *Proc Natl Acad Sci U S A*. 93(20): 10668–10672, 1996.

Vedejs and Peterson, "Stereochemistry and Mechanism in the Wittig Reaction", *Top. Stereochem.*, 21, 1–157, 1994.

Wakabayashi and Mitsuhashi, "In vitro antibacterial activity of AM–1155, a new 6–fluoro–8–methoxy quinolone," *Antimicrob. Agents Chemother.*, 38:594–601, 1994.

Yamada et al., "Quinolone susceptibility of norA–disrupted *Staphylococcus aureus*," *Antimicrob. Agents Chemother.*, 41:2308–2309, 1997.

INHIBITORS OF MULTIDRUG TRANSPORTERS

The present application claims priority to U.S. Provisional Patent Application Serial No. 60/110,841, filed Dec. 4, 1998. The entire text of the above-referenced disclosure is specifically incorporated by reference herein without disclaimer. The government may own rights in the present invention pursuant to grant number GM55449-01 and 1R43AI43076-01 and GM55449–02 from the National Institutes of Health.

BACKGROUND OF THE INVENTION

1. Field of the Invention

The present invention relates generally to the fields of bacteriology and mycology. More particularly, the present invention provides methods and compositions for increasing the effectiveness of existing antibiotics and antifungal agents and methods of overcoming bacterial and fungal resistance.

2. Description of Related Art

Gram positive organisms, particularly Staphylococci, Streptococci, and Enterococci, are increasingly seen as the major aetiological agents in infectious diseases. In the hospital setting, *Staphylococcus aureus* and *Enterococcus faecalis* account for more than 50% of isolates from blood stream infections (Cormican and Jones, 1996). In community-acquired infections *Streptococcus pneumoniae* remains a leading cause of illness and death (Centers for Disease Control, 199). The ongoing and rapid emergence and spread of antibiotic resistance in these organism is thus a problem of crisis proportions.

One of the major impediments in treating Gram-positive infections is their limited susceptibility to fluoroquinolones, the latest addition to the arsenal of antibiotics. Since their introduction in the mid-1980s, fluoroquinolone antibiotics, have become the most used class of antibiotics in the world (Acar and Goldstein, 1997). One such antibiotic., ciprofloxacin (Davis et al., 1996), accounts for 90% of all quinolones used in medicine, Because of its spectrum of activity, oral availability, and relatively low cost. ciprofloxacin has been used for treating a wide range of infections, including those of unknown etiology. In 1996, three new indications for the use of ciprofloxacin were approved suggesting that the use of this antibiotic will continue for many years to come.

Although being highly active against most Gram negative microorganisms ($MIC_{90}$ in the range of 0.1 μg/ml), ciprofloxacin is less effective against Gram positive infections, particularly aerobic Gram positive cocci. The $MIC_{90}$ values for *S. aureus, E. faecalis* and *S. pneumoniae* are in the range of 1–5 μg/ml, whereas the achievable tissue concentration of ciprofloxacin is only 4 μg/ml (Davis et al., 1996). The high intrinsic resistance to ciprofloxacin, and the extensive use of quinolones both in human and veterinary medicine, has led to the emergence and dissemination of ciprofloxacin-resistant Gram-positive strains. This limitation has led to the quest for new, more effective fluoroquinolones.

Antibiotic resistance is mediated, at least in part, by the efflux of drugs from target cells by multidruy transporters (MDTs). These transporters promote the active efflux of a wide variety of drugs, including fluoroquinolone antibiotics, from the bacterial cells that are responsible for the particular infection. In 1991, Neyfakh et al. published the first description of a chromosomally-encoded bacterial multidrug transporter, Bmr, of the Gram positive bacteria *Bacillus subtilis*. Since then, practically every bacterial species analyzed, including pathogenic species such as Escherichia, Pseudomonas, Mycobacteria, etc. (Lomovskaya and Lewis, 1992; Poole et al., 1993; Takiff et al., 1996, reviewed in Nikaido, 1994; Lewis, 1994), has been shown to express one, or even several multidrug transporters. For example, *B subtilis* expresses at least three multidrug transporters, homologous Bmr and Blt (Ahmed et al., 1995) and an evolutionarily more distant Bmr3 (Ohki and Murata, 1997). Bmr and its close homolog in *Staphylococcus aureus*, NorA, promote the efflux of a variety of bacteriotoxic compounds, including ethidium bromide, rhodamine, acridines, tetraphenylphosphonium and puromycin, with fluoroquinolone antibiotics being one of the best transporter substrates (Yoshida et al., 1990; Neyfakh, 1992; Neyfakh et al., 1993). Importantly, drug efflux mediated by the Bmr and NorA transporters can be completely inhibited by the plant alkaloid reserpine, which by itself is not toxic to bacteria (Neyfakh et al.; Neyfakh, 1993).

Multidrug transporters also play an important role in both the intrinsic and acquired resistance of important fungal pathogens to antifuingal agents. Particularly, multidrug transporters contribute to the resistance of *Candida albicans*, the fourth leading cause of all hospital-acquired infections, to azole antifungal agents.

There is little knowledge regarding the physiological role of multidrug transporters or the mechanism of their action; nevertheless these transporters appear to play an important role in the intrinsic resistance of bacterial cells to toxins and antibiotics. Inactivation of the chromosomal transporter genes usually leads to a dramatic increase in the sensitivity of bacteria to the transporter substrates (Poole et al., 1993; Ahmed et al., 1994; Okusu et al., 1996; Yamada et al., 1997). Disruption of the Bmr gene in *B. subtilis*, or the inhibition of the Bmr transporter with reserpine, reduces the minimal inhibitory concentration (MIC) of norfloxacin, a typical fluoroquinolone antibiotic, by a factor of five (Neyfakh, 1992). Similarly, multidrug transporters contribute significantly to the intrinsic fluoroquinolone resistance of Gram positive pathogenic cocci. Yamada et al. (1997) have recently shown that genetic disruption of the NorA gene increases the susceptibility of *S. aureus* to norfloxacin and ciprofloxacin by eight and four fold, respectively. Reserpine, which inhibits NorA-mediated drug efflux, reduces the MIC of norfloxacin for wild-type *S. aureus* by at least four-fold (Markham and Neyfakh, 1996; Kaatz and Seo, 1995). Although the multidrug transporter of *S. pneumoniae* has not yet been identified, its existence is strongly supported by physiological data (Baranova and Neyfakh, 1997; Zeller et al., 1997; Brenwald et al.; 1997). Furthermore, reserpine has been shown to reduce the MIC of norfloxacin and ciprofloxacin for wild-type *S. pneumonae* by the factor of 2–3 (Baranova and Neyfakh, 1997). In *E. faecalis* the active efflux of fluoroquinolones has been demonstrated biochemically (Lynch et al., 1997) and, again, reserpine provides a two-fold increase in their susceptibility to fluoroquinolones.

In addition to being involved in the intrinsic resistance of Gram-positive cocci to fluoroquinolones, multidrug transporters contribute to the acquired resistance, which is selected upon exposure to these antibiotics. In *S. aureus* and *S. pneumoniae*, the acquired resistance has so far been attributed mainly to the sequential acquisition of mutations in the targets of fluoroquinolone action, topoisomerase IV and DNA gyrase (Cambau and Gutman, 1993; Ferrero et al., 1994; Munoz and De La Campa, 1996; Tankovi, 1996). From the limited studies of fluoroquinolone resistance mechanisms in *E. faecalis*, it appears that mutations of gyrase are present in at least some high levet resistant isolates Korten et al., 1994). However, it has become apparent in recent years that these mechanisms of acquired resistance are complemented by over-cxpression of multidrug transporters. Such overexpression can result from either amplification of the transporter gene (Neyfakh, 1991); or mutations in the regulatory regions of these genes or regulatory proteins controlling their transcription (Ahmed et al., 1995; Kaatz and Seo, 1995).

Overexpression of the NorA multidrug transporter has been reported for strains of *S. aureus* selected for fluoroquinolone resistance both in vitro (Yoshida et al., 1990; Kaatz et al., 1990) and in vivo (Trucksis et al., 1991). From the discussion above it is clear that multidrug transporters present a major impediment to the treatment of Gram positive pathogenic insult. There exists a need for drug(s) that may circumvent these transporters to be useful in treatment regimens.

SUMMARY OF THE INVENTION

In order to meet the objectives of the present invention, there are provided methods of enhancing the antimicrobial action of antimicrobial agents by inhibiting the multidrug transporters in the microbes. A specific embodiment of the present invention contemplates a method for enhancing the antibacterial action of fluoroquinolones comprising contacting a bacterium with an inhibitor of NorA, wherein said inhibitor is an indole, a urea, an aromatic amide or a quinoline.

In more particular embodiments, the inhibitor is an indole that has the general formula:

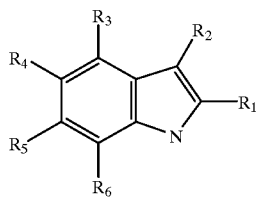

(I)

wherein $R_1$ is phenyl, 2-naphthyl, o-anisole, $R_2$ is H or $CH_3$, $R_1$ and $R_2$ are two naphthyl groups fused to the indole ring, $R_3$ is H, $R_4$ is $NO_2$, $SO_3H$, $NH_2$ and $CF_3$ or $CCl_3$, $R_5$ is H, and $R_6$ is H. More particularly, the $R_1$ may be a phenyl group and $R_4$ may be $SO_3H$ or $NO_2$. In other specifically preferred embodiments, the $R_1$ may be 2-naphthyl and $R_4$ may be $CCl_3$ or $CF_3$. In still additional embodiments, the $R_1$ may be o-anisole and $R_4$ may be $NO_2$. In further embodiments, the $R_1$ and $R_2$ are two naphthyl groups fused to the indole ring. Additional preferred embodiments are contemplated in which $R_1$ is phenyl and $R_2$ is $CH_3$.

In those aspects of the invention in which the inhibitor is a urea, the urea may have the general formula:

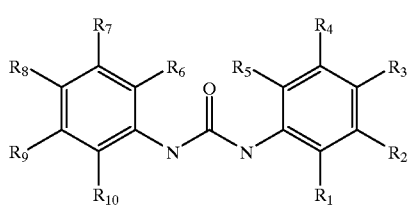

(II)

wherein $R_1$ is OR, Br, Cl, or F, $R_2$ is OR, $NHCO_2$ R, Cl, F, or H, $R_3$ is Cl, Br, OR, or $CO_2R$, $R_4$ is Cl or Br, $R_5$ is H, $R_6$ is H, $R_7$ is H, $R_8$ is a conjugated or aromatic system. $R_9$ is H, OR, Cl or Br, $R_{10}$ is H, OR, or Cl. More particularly, $R_1$ may be OMe, and either $R_3$ or $R_4$ may be Cl, in addition to $R_8$ being C(=O)Ph or a fused aromatic ring at $R_7$ –$R_8$.

In those embodiments in which the inhibitor is an aromatic amide, the inhibitor may have the general formula:

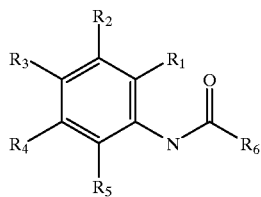

(III)

wherein $R_1$, $R_4$ and $R_5$ are H, $R_2$ and/or $R_3$ are small electron-withdrawing groups, and $R_6$ is a substituted or unsubstituted alkyl of at least six atoms including O, N or S, with or without a phenyl ring. More particularly, the electron-withdrawing group is selected from the group consisting of Cl, and F. In other preferred embodiments, the $R_4$ and $R_6$ in the aromatic amide of structure III are smaller conjugated systems of 2–6 atoms of C, O, N or S, and includes a phenyl ring.

In those embodiments in which the inhibitor is a quinoline, the inhibitor may have the general formula:

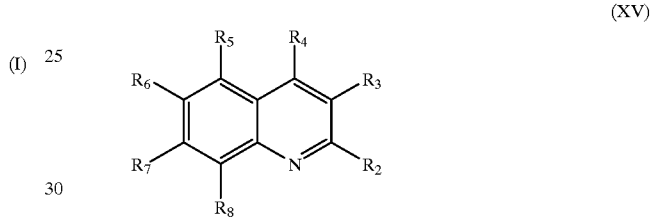

(XV)

wherein $R_2$ may be 3, 4-dimethoxybenzene or p-toluene, $R_3$ is H, $R_4$ may be $CO_2R$, C(=O)NH2, or H , $R_5$ is H, $R_6$ is H , $NO_2$, $SO_3H$, $NH_2$, $CF_3$ or $CCl_3$, $R_7$ is an alkyl group, $NO_2$, $SO_3H$, $NH_2$, $CF_3$ or $CCl_3$ and $R_8$ is H. In particular, the combination where $R_2$ is 3, 4-dimethoxybenzene, $R_3$ is H, $R_4$ is $CO_2R$ , $R_5$ is H, $R_6$ is H , $R_7$ is Me, and $R_8$ is H.

It is particularly contemplated that the bacterium is *Streptococcus pneumonia, Enterococcus faecalis, Staphylococcus aureus, Streptococcus pyogenes, Escherichia coli, Pseudomonas aeruginosa, Staphylococcus epiderimis, Mycobacterium smegmatis* and *Serratia marcesens*. Of course, those of skill in the art will realize that the inhibitors found to be useful in applications against these bacteria also may be useful against other bacterial infections. As such these are exemplary bacteria and the present invention is not intended to be limited to infection caused by these bacteria.

Another aspect of the present invention provides an indole having the general formula:

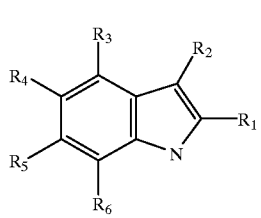

(I)

wherein $R_1$ is phenyl, 2-naphthyl, o-anisole, $R_2$ is H or $CH_3$, $R_1$ and $R_2$ are two naphthyl groups fused to the indole ring, $R_3$ is H, $R_4$ is $NO_2$, $SO_3H$, $NH_2$ and $CF_3$ or $CCl_3$, $R_5$ is H , and $R_6$ is H. In specific embodiments, $R_1$ is phenyl and $R_4$ is $SO_3H$ or $NO_2$. In other embodiments, $R_1$ is 2-naphthyl and $R_4$ is $CCl_3$ or $CF_3$. In still additional embodiments, $R_1$ is o-anisole and $R_4$ is $NO_2$. Other embodiments contemplate an indole in which $R_1$ and $R_2$ are two naphthyl groups fused to the indole ring. Yet another indole molecule contemplated is one in which $R_1$ is phenyl and $R_2$ is $CH_3$.

Also contemplated herein is a urea having the general formula:

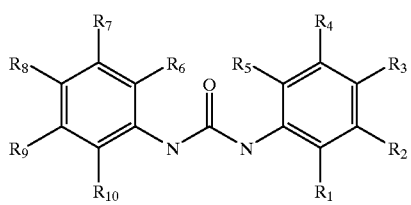

(II)

wherein $R_1$ is OR, Br, Cl, or F, $R_2$ is OR, $NHCO_2R$, Cl, F, or H, $R_3$ is Cl, Br, OR, or $CO_2R$, $R_4$ is Cl or Br, $R_5$ is H, $R_6$ is H, $R_7$ is H. $R_8$ is a conjugated or aromatic system, $R_9$ is H, OR, Cl or Br, $R_{10}$ is H, OR, or Cl. More particularly, $R_1$ may be OMe, and either $R_3$ or $R_4$ may be Cl, in addition to $R_8$ being C(=O)Ph or a fused aromatic ring at $R_7$–$R_8$.

Also contemplated herein is an aromatic amide having the general formula:

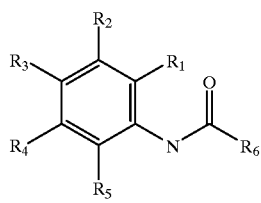

(III)

wherein $R_1$, $R_4$ and $R_5$ are H; $R_2$ and/or $R_3$ are small electron withdrawing groups, and $R_6$ is substituted or unsubstituted alkyl of at least six atoms including C, O, N or S, with or without a phenyl ring. Specifically the aromatic amide may be one in which $R_4$ and $R_6$ are smaller conjugated systems of 2–6 atoms of C, O, N or S, and includes a phenyl ring.

Another aspect of the present invention provides a quinoline having the general formula:

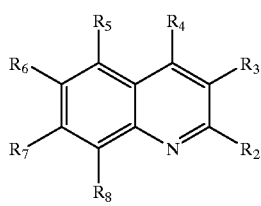

(XV)

wherein $R_2$ may be 3, 4-dimethoxybenzene or p-toluene, $R_3$ is H, $R_4$ may be $CO_2R$, C(=O)NH2, or H, $R_5$ is H, $R_6$ is H, $NO_2$, $SO_3H$, $NH_2$, $CF_3$ or $CCl_3$, $R_7$ is an alkyl group, $NO_2$, $SO_3H$, $NH_2$, $CF_3$ or $CCl_3$ and $R_8$ is H. In particular, the combination where $R_2$ is 3, 4-dimethoxybenzene, $R_3$ is H, $R_4$ is $CO_2R$, $R_5$ is H, $R_6$ is H, $R_7$ is Me, and $R_8$ is H.

Another aspect of the present invention contemplates a method of screening for inhibitors of NorA comprising providing a cell expressing only a single functional transporter, said transporter being Nor A; contacting said cell with a transportable element in the presence of a candidate inhibitor substance; and comparing the transport of said element by said cell with the transport of said element in the absence of said candidate inhibitor substance.

In particularly preferred embodiments, the cell is a bacterial cell. In additional preferred embodiments, the bacterial cell is a Gram negative bacterial cell. In other preferred embodiments, the bacterial cell is a Gram positive bacterial cell. More particularly, the Gram positive bacterial cell is a *Bacillus subtilis* cell. In specific embodiments, it is contemplated that the *B. subtilis* cell contains disrupted Bmr and Blt genes.

In other preferred embodiments it is contemplated that the NorA is *Staphylococcus aureus* NorA, *Streptococcus pneumoniae* multidrug transporter, or *Enterococcus faecalis* multidrug transporter. In particular embodiments the transportable element is ethidium bromide. In other embodiments, the transportable element is a fluoroquinolone.

Another aspect of the present invention provides a method for treating a subject with a bacterial infection comprising providing to said subject a fluoroquinolone and an inhibitor of NorA, wherein said inhibitor is an indole, a urea or an aromatic amide. In preferred embodiments, the bacterium is *Streptococcus pneumonia, Enterococcus faecalis, Staphylococcus aureus, Streptococcus pyogenes, Escherichia coli, Pseudomonas aeruginosa, Staphylococcus epidermis, Mycobocterium smegmatis* and *Serratia marcesens*

Also provided herein is a pharmaceutical composition comprising a fluoroquinolone and an inhibitor of NorA, wherein said inhibitor is an indole, a urea or an aromatic amide. In certain embodiments, the fluoroquinolone is selected from the group consisting of Sparfloxacin, Levofloxacin, Grepafloxacin, Temafloxacin, Clinafloxacin, Bay 12- 8039, Trovafloxacin, DU6859a, Sarafloxacin. In addition to the fluoroquinolones, it is contemplated that other quinolones such as fluoronaphthyridones may be useful in the compositions of the present invention. A particularly preferred quinolone is LB20304. Of course, one of skill in the art will realize that there will be other antibacterial fluoroquinolones that may be combined with the inhibitors of the present invention. As such, the present invention is not limited for use in compositions with the listed fluoroquinolones alone, rather the inhibitors will be useful in combination with any fluoroquinolone or other agent that possesses antibacterial activity. Additionally, the inhibitors of the present invention will be useful with any antibacterial agent which is or would be effective at killing, reducing or otherwise diminishing the growth of bacteria but for the presence of resistance created by the multidrug transporters in such bacteria.

Another aspect of the present invention describes a method of enhancing the antifungal action of azole antifungal agents comprising contacting a fungus with an inhibitor of a fungal multidrug transport protein, wherein said inhibitor is an indole, a urea, an aromatic amide or a quinoline. More particularly. the indole has the general formula I, the urea has the general formula II, the aromatic amide has the general formula III and the quinoline has the general formula XV. It is particularly contemplated that the fungus is from a species selected from the giroup consisting of Candida, Cryptococcus, Blastomyces, Histoplasma, Torulopis, Coccidioides, Paracoccidioides and Asperugillis. Of course one of skill in the art will realize that the invention is not limited to only treating these fungal infections but rather that the inhibitors will likely be useful against many other fungal species.

Yet another embodiment of the present invention provides a method of screening for inhibitors of a fungal multidrug transporter comprising: providing a cell expressing only a single functional transporter, said transporter being fungal multidrug transporter; contacting said cell with a transportable clement in the presence of a candidate inhibitor substance; and comparing the transport of said element by said cell with the transport of said element in the absence of said candidate inhibitor substance. In specific embodiments, the cell is a fungal cell.

In specifically preferred embodiments, the cell is from the Candida species. In other preferred embodiments, the multidrug transporter is a Candida multidrug transporter. In certain embodiments, the antifungal agent is a triazole antifungal agent. In other preferred embodiments, the triazole is selected from the group consisting of ketoconazole, miconazole, itraconazole, fluconazole, griseofluconazole, clotrimazole. econazole, terconazole and butaconazole. It should be understood that these triazole anti-fungal agents are exemplary agents, additional azoles also may be useful in the present invention. Such additional azoles may be derived form these azoles listed or have a similar mode of action to these compounds.

Another aspect of the present invention provides a method of treating a subject with a fungal infection comprising providing to said subject an azole antifungal agent and an inhibitor of a fungal multidrug transport protein, wherein said inhibitor is an indole, a urea, an aromatic amide or a quinoline. In specific embodiments, the antifungal agent is selected from the group consisting of ketoconazole, miconazole, itraconazole, fluconazole, griseofluconazole, clotrimazole, econazole, terconazole and butaconazole.

Also provided herein is a pharmaceutical composition comprising an azole antifungal agent and an inhibitor of a fungal multidrug transporter, wherein said inhibitor is an indole, a urea, or an aromatic amide.

Other objects, features and advantages of the present invention will become apparent from the following detailed description. It should be understood however, that the detailed description and the specific examples, while indicating preferred embodiments of the invention, are given by way of illustration only, since various changes and modifications within the spirit and scope of the invention will become apparent to those skilled in the art from this detailed description.

BRIEF DESICRIPTION OF THE DRAWINGS

FIG. 1. CoMFA contour map for the indole sterie field. INF55 is pictured within this field. Green areas indicate favored regions of bulk and yellow indicates unfavorable regions for bulky groups.

Figure 2:
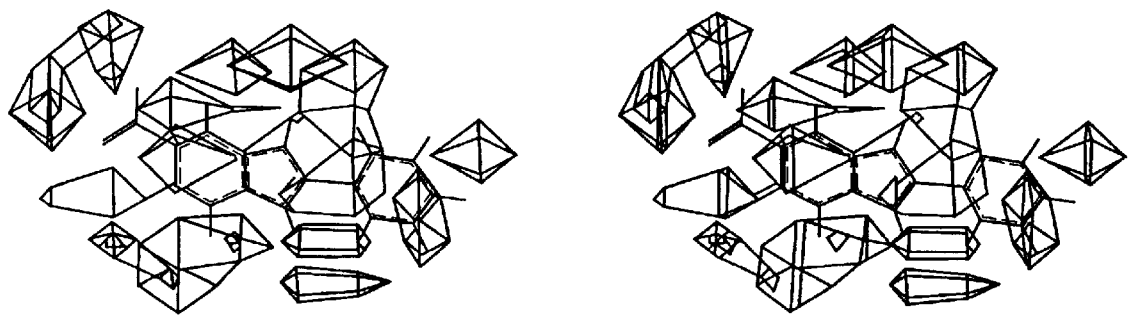

FIG. 2. CoMFA contour map for the indole electrostatic field. INF55 is pictured within this field. Red areas indicate favored regions of negative charge and blue indicates favored regions of positive charge.

Figure 3:
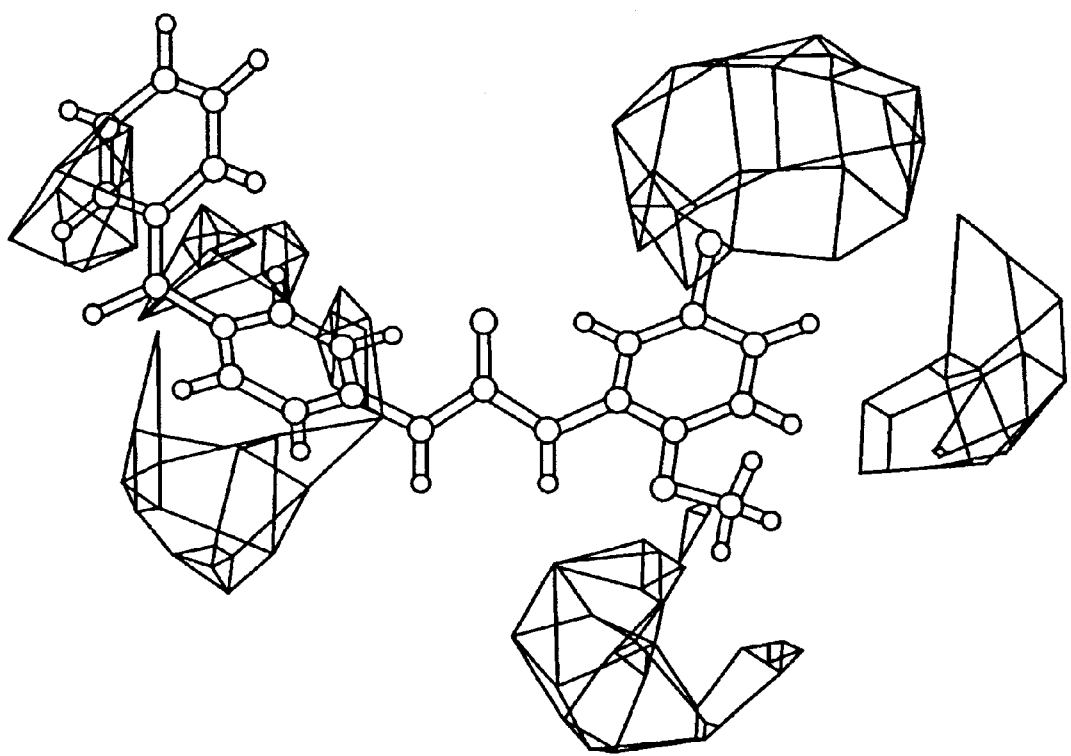

FIG. 3. CoMFA contour map for the biphenyl urea steric field. INF271,276, is pictured within this field. Green areas indicate favored regions of bulk and yellow indicates unfavorable regions for bulky groups.

Figure 4:
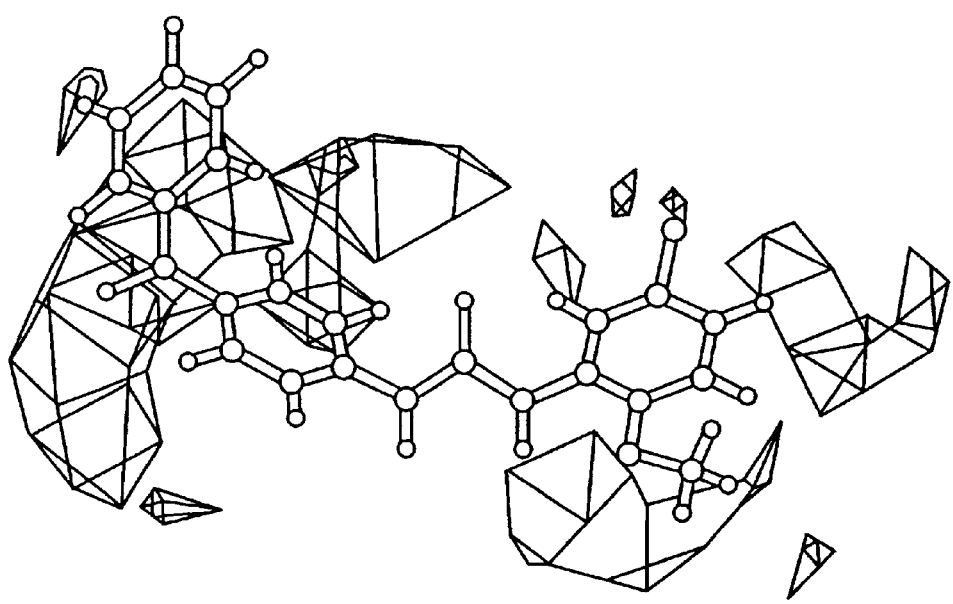

FIG. 4. CoMFA contour map for the biphenyl urea electrostatic field. INF271, 276 is pictured within this field. Red areas indicate favored regions of negative charge and blue indicates favored regions of positive charge.

Figure 5:
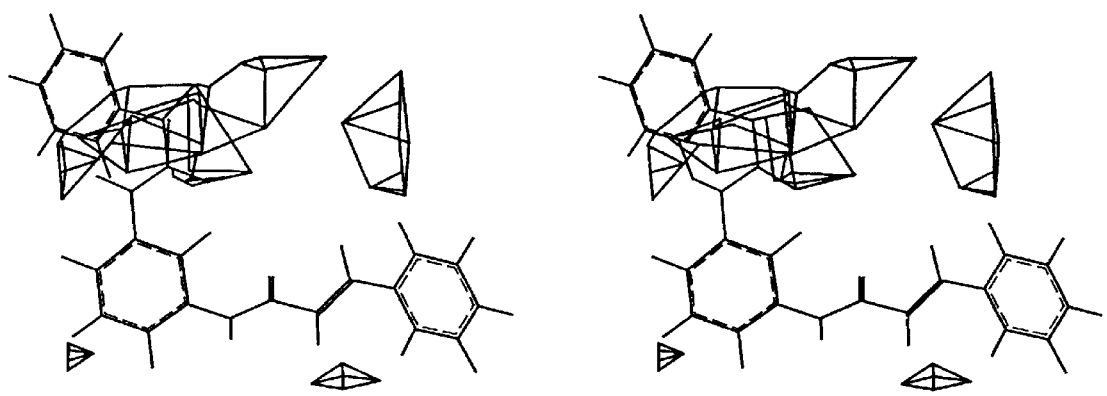

FIG. 5. CoMFA contour map for the aromatic amide steric field. INF240 is pictured within this field. Green areas indicate favored regions of bulk and yellow indicates unfavorable regions for bulky groups.

Figure 6:
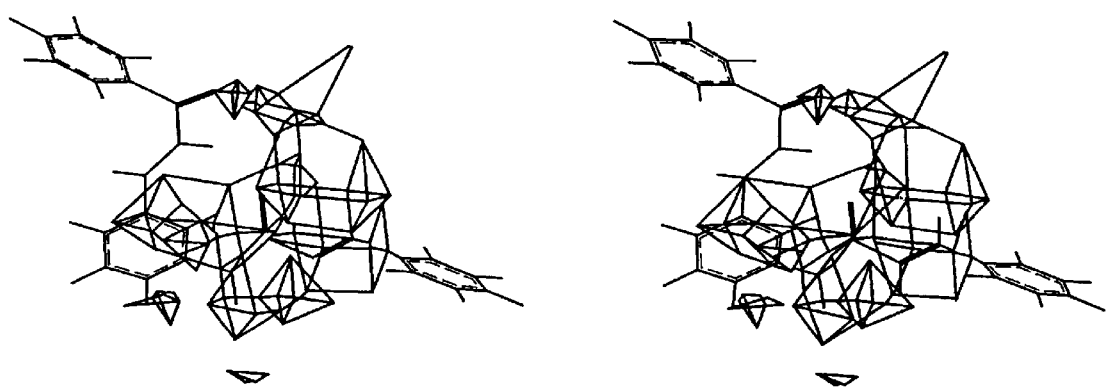

FIG. 6. CoMFA contour map for the aromatic amide electrostatic field. INF240 is pictured within this field. Red areas indicate favored regions of negative charge and blue indicates favored regions of positive charge.

Figure 7:
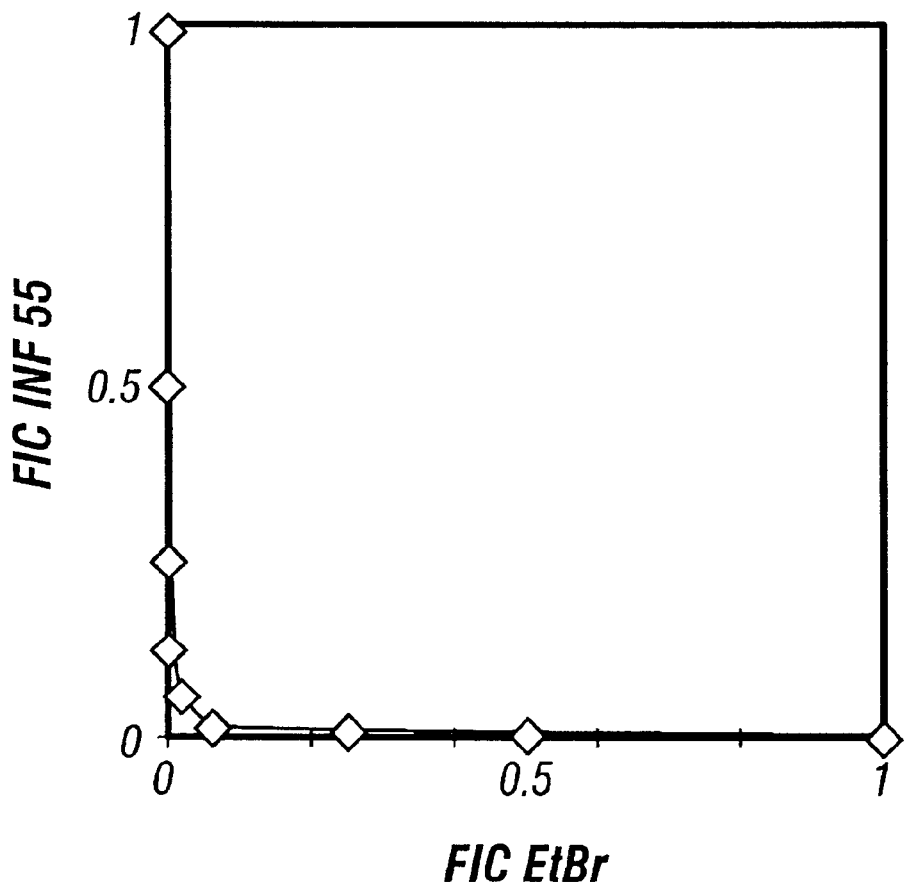

FIG. 7. Synergy curve for the combination of INF 55 with ethidium.

Figure 8:
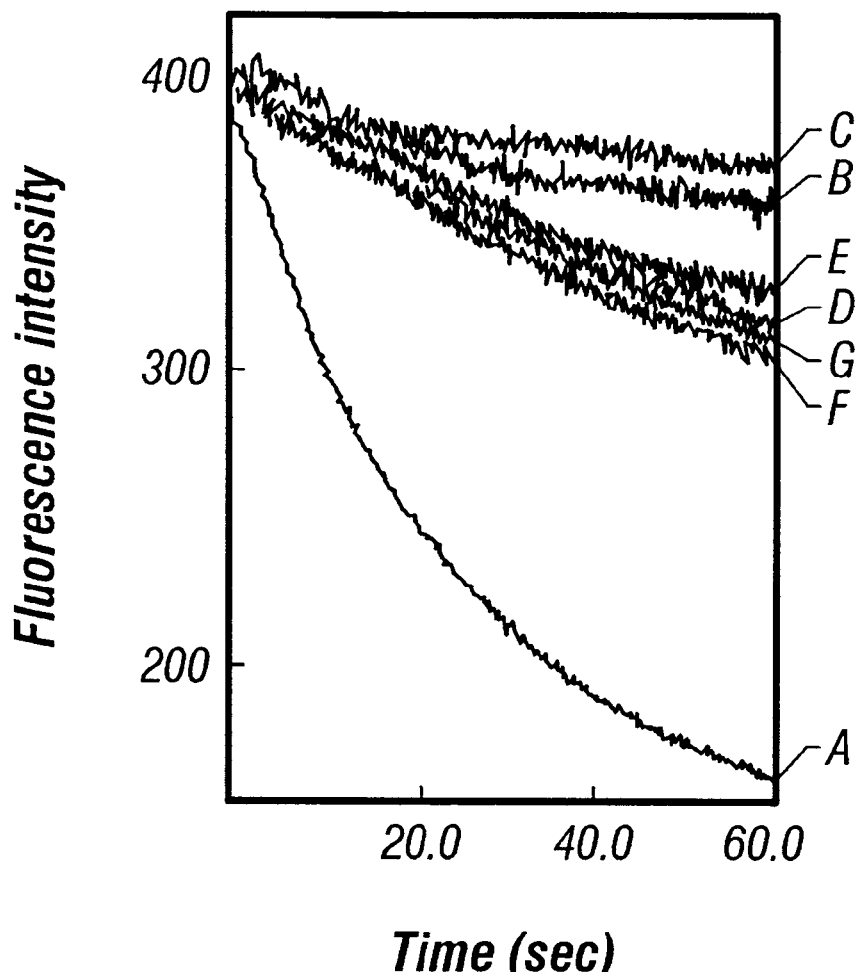

FIG. 8. Effect of the lead inhibitors on ethidium efflux from NA cells. NA cells were loaded with ethidium in the presence of reserpine and allowed to efflux in the absence of reserpine (A) in the presence of 20 $\mu$g/ml reserpine (B), 5 $\mu$g/ml of INF 55 (C), 5 $\mu$g/ml of INF 240 (D), 5 $\mu$g/ml of INF 271 (E), 5 $\mu$g/ml of INF 392 (F), or 10 $\mu$g/ml of INF 277 (G). Fluorescence intensity is proportional to the amount of ethidium remaining inside the cells.

Figure 9:
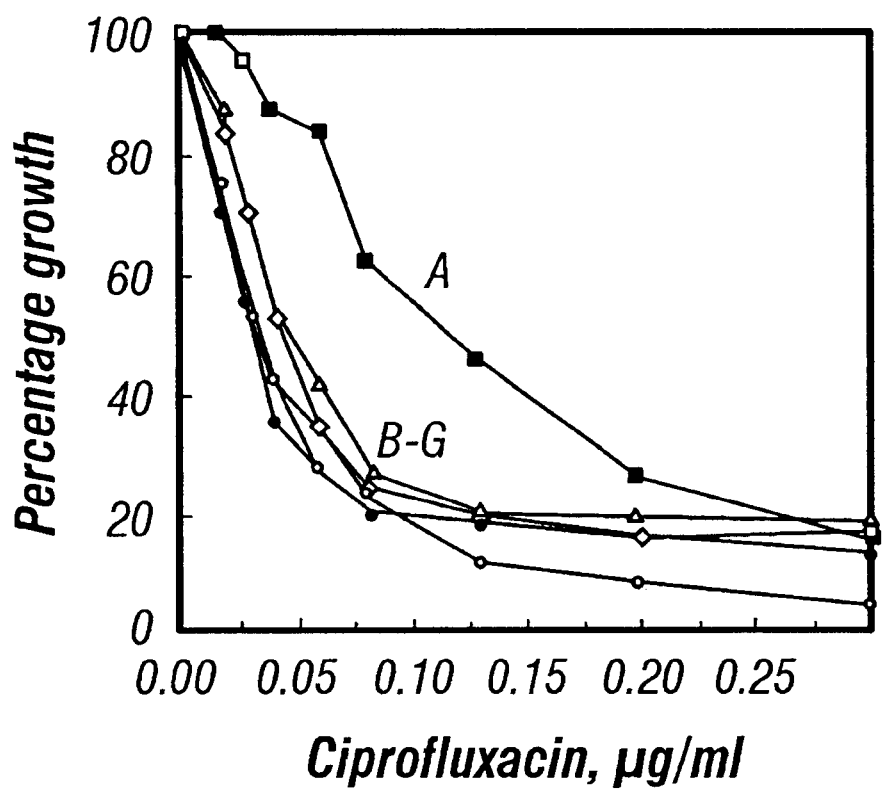

FIG. 9. Effect of the lead inhibitors on the susceptibility of wild type S. aureus (SA1199) to ciprofloxacin. Cells were diluted to an $OD_{600}$ of 0.01 into tubes with LB medium containing different concentrations of ciprofloxacin (1.5 fold dilutions) and no inhibitor(A), 20 $\mu$g/ml reserpine (B), 5 $\mu$g/ml INF 55 (C), 5 $\mu$g/ml INF 240 (D) 5 $\mu$g/ml INF 271 (E), 1.25 $\mu$g/ml INF 277 (F), 1.25 $\mu$g/ml INF 392 (G). Optical densities were determined after 3 h incubation.

DESCRIPTION OF ILLUSTRATIVE EMBODIMENTS

The development of clinically useful inhibitors of the multidrug-efflux transporters in Gram positive pathogenic bacteria, *Staphylococcus aureus* and *Streptococcus pneumoniae*, is essential if these opportunistic Gram positive infections are to be effectively treated. As stated above, Gram positive infections are notoriously difficult to treat. One major impediment to the effective treatment of Gram positive infections is antibiotic resistance that is mediated by multidrug transporters. These transporters are involved in both intrinsic and acquired resistance to fluoroquinolone antibiotics. Staphylococci and Pneumococci, two pathogens of enormous clinical importance, are particularly retractile to fluoroquinolone therapy. Further, it is known that fungal pathogens also have multidrug transporters that share significant homology with NorA. The present application demonstrates that inhibition of the multidrug transporters in bacterial pathogens would dramatically increase the effectiveness of fluoroquinolone therapy by both increasing the intrinsic susceptibility of these pathogens to fluoroquinolones and suppressing the emergence of drug-resistant variants. Furthermore, the inhibitors identified herein as active against NorA also are likely to show cross reactivity with fungal multidrug transporters and prove useful in potentiating the antifungal effects of azole antifungal agents by decreasing intrinsic or acquired azole resistance.

The present invention shows that the use of fluoroquinolones in combination with an inhibitor of multidrug transporters dramatically improves the antibacterial efficacy of these antibiotics by both reducing their effective concentration several fold (shifting it well below their practically achievable tissue levels) and preventing the emcrgence of drug-resistant variants. These inhibitors also may be useful in antifungal applications.

Prior to the present invention, reserpine was the only known inhibitor of bacterial multidrug transporters. Unfortunately, reserpine cannot be used to potentiate fluoroquinolones because of its neurotoxicity at the required concentrations. The inventors have demonstrated the feasibility of developing alternative inhibitors and identified a number of structurally diverse lead compounds that are highly active against multidrug transporters of both *S. aureus* and *S. pneumoniae*. This cross-species activity of the newly identified inhibitors is very encouraging. In the majority of clinical cases, e.g., pneumonia, otitis media, etc. physicians frequently are forced to treat patients without knowing the biological nature of a pathogen. The present invention provides an array of powerful broad spectrum inhibitors of potentially very broad clinical usefulness.

1. The Present Invention

The inventors have screened a library of synthetic chemicals and identified several promising lead compounds that effectively inhibit the S. aureus multidrug transporter NorA. Some of these lead compounds also were found to be effective against the presently unidentified multidrug transporter of Streptococcus pneumoniae.

A library of compounds was screened and 399 compounds were suggested as potential inhibitors. Of these 399, 54 showed activity at 5 µg/mL or less, while the others showed moderate to little activity at 10–20 µg/mL. Three of the most potent compounds are shown below as INF55 with an indole moiety; a urea compound, INF271; and INF240, possessing an aromatic amide functional group. Since it is unclear whether NorA has more than one potential binding site, the compounds were subdivided into the three groups: indoles (nitroindoles), the ureas, and the aromatic amides. These three classes of compounds were evaluated using the activity data provided, and the CoMFA fields generated to see if a 3D-QSAR relationship was present.

Structures of IFN55, INF271 and INF240

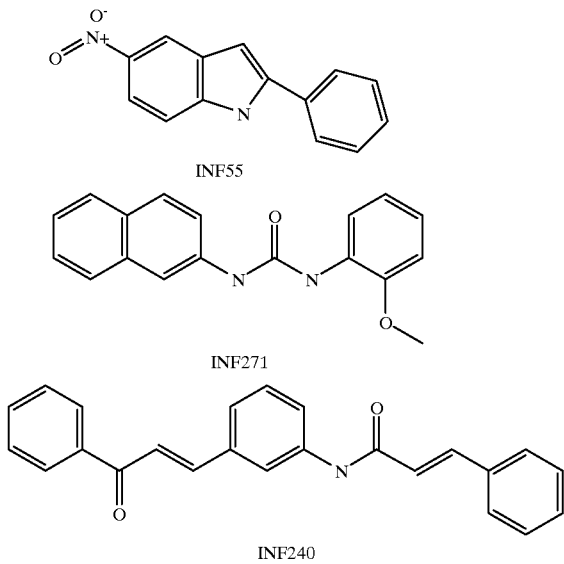

Using the insights gained from the analyses performed, the present invention provides methods for enhancing the antibacterial action of fluoroquinolones comprising contacting bacteria with an inhibitor of NorA in combination with the fluoroquinolone therapy. The inhibitor may therefore be an indole, a urea or an aromatic amide. More particularly, the indole will have a generic formula (I) in which $R_1$ is phenyl, 2-naphthyl or o-anisole, $R_2$ is H, or $CH_3$, $R_1$ and $R_2$ are two naphthyl groups fused to the indole ring, $R_3$ is H, $R_4$ is $NO_2$, $SO_3H$, $NH_2$ and $CF_3$ or $CCl_3$, $R_5$ is H, and $R_6$ is H.

(I)

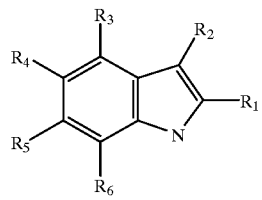

In a particular example of the indole used in the present invention, R1 is a phellyl group and $R_4$ is an $SO_3H$ group (structure IV); in another example the indole has a phenyl group at $R_1$ and an $NO_2$, group at R4 (structure V). Structure VI shows an indole of the present invention in which $R_1$ is 2-naphthyl and $R_4$ is $CCl_3$, the indole of structure VII has 2-naphthyl at $R_1$ and $CF_3$ at $R_4$. Structure VIII shows an indole of the present invention in which $R_1$ is o-anisole and $R_4$ is $NO_2$. Yet another indole of the present invention has a naphthyl groups fused to the indole rings (structure IX). Also contemplated to be useful in the present invention is a structure wherein $R_1$ is phenyl and $R_2$ is $CH_3$ (structure X), a more particularly defined indole having this structure is shown in structure XI, in which R4 is further defined as an $NO_2$ group. Of course these are exemplary indoles of the present invention, additional indoles may be useful as and described herein.

(IV)

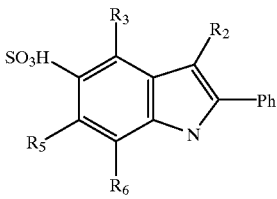

(V)

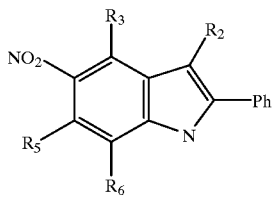

(VI)

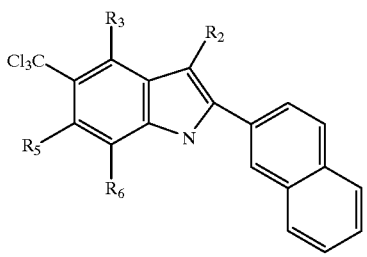

(VII)

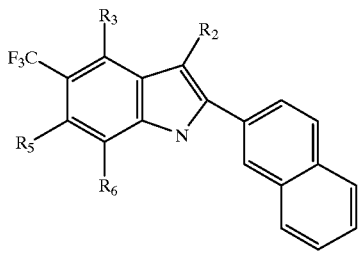

(VIII)

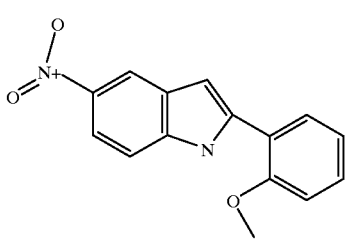

-continued

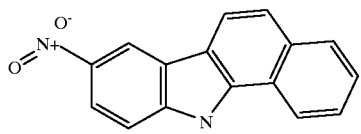
(IX)

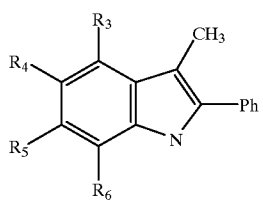
(X)

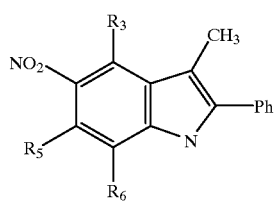
(XI)

In specific embodiments of the present invention the inhibitor is a urea having the general formula:

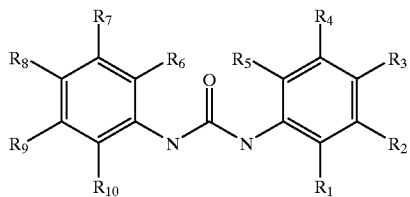
(II)

wherein $R_1$ is OR, Br, Cl, or F, $R_2$ is OR, NHCO$_2$R Cl, F, or H, $R_3$ is Cl, Br, OR, or CO$_2$R, $R_4$ is Cl or Br, $R_5$ is H, $R_6$ is H, $R_7$ is H, $R_8$ is a conjugated or aromatic system. $R_9$ is H, OR, Cl or Br, $R_{10}$ is H, OR, or Cl. More particularly the present invention contemplates a biphenyl urea where $R_1$ is OMe, and either $R_3$ or $R_4$ may be Cl, in addition to $R_8$ being C(=O)Ph, a fused aromatic ring at $R_7$–$R_8$, or a Ph at $R_7$. In other examples, $R_1$ is OMe, $R_4$ is Cl, and $R_9$ is OR, Br, or I. Certain examples also have a urea (II) with $R_2$ and $R_3$ being Cl, and $R_8$ being C(=O)Ph, or $R_1$ and $R_4$ being Cl, or $R_9$, being OR.

In specific embodiments, the inhibitor is an aromatic amide that has the general formula:

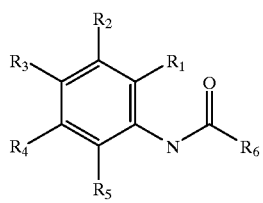
(III)

wherein $R_1$, $R_4$ and $R_5$ are H, $R_2$ and/or $R_3$ are small electron-withdrawingy groups, and $R_6$ is substituted or unsubstituted alkyl of at least six atoms including O, N or S, with or without a phenyl ring. More particularly, the electron-withdrawing group may be a Cl or an F moiety. Other aromatic amides of the present invention have smaller conjugated systems of 2–6 atoms of C, O, N or S at $R_4$ and $R_6$, and include a phenyl ring.

In other embodiments, the inhibitor is a quinoline that has the general formula:

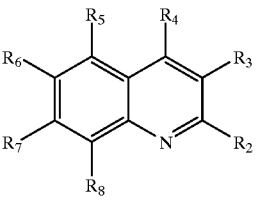
(XV)

wherein $R_2$ may be 3, 4-dimethoxybenzene or p-toluene, $R_3$ is H, $R_4$ may be CO$_2$R, C(=O)NH2, or H, $R_5$ is H, $R_6$ is H, NO$_2$, SO$_3$H, NH$_2$, CF$_3$ or CCl$_3$, $R_7$ is an alkyl group, NO$_2$, SO$_3$H, NH$_2$, CF$_3$ or CCl$_3$, and is H$_8$. In particular, the combination where $R_2$ is 3, 4-dimethoxybenlzene, $R_3$ is H, $R_4$ is CO$_2$R, $R_5$ is H, $R_6$ is H, $R_7$ is Me, and $R_8$ is H.

The present specification shows that the above compounds are useful in combinations with fluoroquinolones in the treatment of bacterial and more particularly Gram positive bacterial infections. These compounds also may be useful in anti-fungal applications. Method and compositions for the production and/or screening for the activities of these compounds are discussed in further detail herein below. Similarly, these compounds may be used as lead compounds for generating additional compounds that will be useful as inhibitors of multidrug transporters in bacterial and fungal pathogens.

2. Drug Efflux Proteins in Multidrug Resistant Bacteria

Bacteria contain an array of transport proteins in their cytoplasmic membrane. Many of these proteins play an important role in conferring intrinsic and acquired resistance to toxic compounds. Several chromosomally encoded multidrug transporters have been identified in Gram positive bacteria including Bmr (Neyfakh et al., 1991). Blt (Ahmed et al., 1995), Bmr3 (Ohki and Murata, 1997) in *Bacillus subtilis*, NorA in *Staphylococcus aureus* (Neyfakh et al., 1993; Yoshida et al., 1990), LmrP (Bolhuis et al., 1995) and LmrA (van Veen et al., 1996) in *Lactobacillus lactis* and LfrA in *Mcyobacteriaum smegmatis* (Takiff et al., 1996).

One of the most effective regimens for controlling Gram negative infections employs fluoroquinolone compounds. One Such compound, ciprofloxacin (Davis et al., 1996) accounts for 90% of all quinolones used in medicine (Acar and Goldstein, 1997). Because of its spectrum of activity, oral availability, and relatively low cost. ciprofloxacin has been used for treating a wide range of infections, including those of unknown etiology. Although it is highly active against most Gram negative microorganisms (MIC$_{90}$ in the range of 0.1 μg/ml), ciprofloxacin is much less effective against Gram positive infectious. particularly aerobic Gram positive cocci. The MIC$_{90}$ values for *S. aureus, E. faecalis* and *S. pneumoniae* are in the range of 1–5 μg/ml, whereas the achievable tissue concentration of ciprofloxacin is only 4 μg/ml (Davis et al., 1996). The high intrinsic resistance to ciprofloxacin and the extensive use of quinolones both in human and veterinary medicine has led to the emergence and dissemination of ciprofloxacin-resistant Gram-positive strains. This resistance is thought to be due to the presence of specific multidrug transporters in the Gram positive bacteria.

In addition to being involved in the intrinsic resistance of Gram-positive cocci to fluoroquinolones, multidrug transporters contribute to the acquired resistance, which is selected upon exposure to these antibiotics. In *S. aureus* and *S. pneumoniae*, the acquired resistance has so far been attributed mainly to the sequential acquisition of mutations in the targets of fluoroquinolone action, topoisomerase IV and DNA gyrase (Cambau and Gutman, 1993; Ferrero et al., 1994; Munoz and De La Campa, 1996; Tankovi. 1996). From the limited studies of fluoroquinolone resistance mechanisms in *E. faecalis*, it appears that mutations of gyrase are present in at least some high levet resistant isolates Korten et al., 1994). However, it has become apparent in recent years that these mechanisms of acquired resistance are complemented by over-expression of multi-drug transporters. Such over-expression can result from either amplification of the transporter gene (Neyfakh, 1991); or mutations in the regulatory regions of these genes or regulatory proteins controlling their transcription (Ahmed et al., 1995; Kaatz and Seo., 1995).

NorA is a multidrug transporter involved in both the intrinsic and acquired resistance of the pathogen *Staphylococcus aureus* to a variety of unrelated compounds including a number of widely used fluoroquinolone antibiotics, by means of their active extrusion from the bacterial cell. ihe present invention identifies and characterizes numerous inhibitors of NorA.

The inventors' recent studies indicate that a multidrug efflux mechanism also appears to contribute to the intrinsic and acquired fluoroquinolone resistance of *Streptococcus pneumoniae*, another clinically important Gram positive pathogen which has only a moderate susceptibility to ciprofloxacin ($MIC_{90}$ 1–2 $\mu g/ml$). The present invention shows that some of the most active NorA inhibitors are also effective in promoting, ciprofloxacin bacteriotoxicity in *S. pneumoniae*. The inventors suggest that the lead inhibitors will also be effective in promoting fluoroquinolone bacteriotoxicity, not only in *S. aureus*, but also in *S. pneumoniae* and *E. faecalis*. The following section summarizes the recent findings supporting the involvement of a multidrug efflux mechanism in the ciprofloxacin resistance of *S. pneumoniae*.

The present inventors recently reported the presence of an efflux-dependent fluoroquinolone resistance mechanism in *S. pneumoniae* selected for increased resistance to ethidium bromide (Baranova and Neyfakh, 1997). Ethidium resistance in the selected strain, called EBR, was shown to result from increased efflux of this drug. EBR also demonstrates increased resistance to the fluoroquinolones ciprofloxacin and norfloxacin, suggesting the contribution of a multidrug efflux transporter, tentatively termed PmrA. Although no cross resistance of this strain to the Bmr and NorA substrate rhodamine was observed, reserpine, at non-toxic concentrations, inhibited ethidium efflux and reversed the resistance to both ethidium and fluoroquiniolones. Furthermore, reserpine was shown to potentiate the susceptibility of wild type *S. pneumoniae* to ethidium and fluoroquinolones by two to three fold. This suggests that, like other multidrug transporters in Gram positive bacteria, this efflux mechanism may contribute to the intrinsic and acquired resistance of *S. pneumoniae* to fluoroquinolone antibiotics.

Analogous to *S. aureus*, mutations in topoisomerase IV precede mutations in gyrase in stepwise selected ciprofloxacin-resistant mutants of *S. pneumoniae* (Tankovic et al., 1996). However, unlike *S. aureus*, there appears to be an additional stage that precedes the acquisition of mutations in topoisomerase IV, namely, selected cells demonstrate elevated fluoroquinolone resistance with no detectable mutations in the topoisomerase or gyrase genes (Tankovic et al., 1996). The inventors speculated that fluoroquinolone resistance at this stage may result from the increased expression of the putative multidrug efflux transporter PmrA, and thus, not only would such mutants exhibit cross resistance to ethidium bromide but also that reserpine would decrease their augmented drug resistance. To investigate this possibility, the inventors selected in vitro first step mutants of *S. pneumoniae* (ATCC 49619), resistant to four-fold the MIC of ciprofloxacin (2 $\mu g/ml$). Selection of $10^9$ cells yielded fifteen such mutants, of which three were analyzed further. Compared to the parental strain, all three mutants exhibited an eight-fold increase in the ciprofloxacin MIC. Interestingly, the MIC of ethidium bromide for these three mutants also increased, by 8–16 fold. Furthermore, a non-toxic concentration of reserpine reversed the resistance to both ciprofloxacin and ethidium bromide. Similar to the EBR strain, no increase in resistance to rhodamine was observed, suggesting the involvement of the same transporter, PmrA.

These data indicate that a multidrug efflux transporter not only contributes to the intrinsic fluoroquinolone susceptibility of *S. pneumoniae*, but also mediates resistance to fluoroquinolones in first step mutants of this pathogen. Supporting this notion, Zeller et al. (1997) recently reported that a first step in vitro selected ciprofloxacin resistant mutant of *S. pneumoniae* which had no alterations in Topo IV, exhibited increased efflux of ciprofloxacin and a drug resistance profile resembling that conferred by NorA expression.

Multidrug transporters also play an important role in both the intrinsic and acquired resistance of important fungal pathogens to antifungal agents. Particularly, multidrug transporters contribute to the resistance of *Candida albicans*, the fourth leading cause of all hospital-acquircd infections, to azolc antifungal agents. A number of these fungal multidrug transporters belong to the major facilitator superfamily of membrane transporters and share significant homology with NorA. The inhibitors identified as active against NorA are highly likely to show cross reactivity with fungal multidrug transporters and prove useful in potentiatinig the antifuingal effects of azole antifungal agents by decreasing intrinsic or acquired azole resistance.

3. Chemical Synthesis of Diverse Analogs of the Lead Inhibitors.

As described elsewhere herein, the inventors have a substantial database of compounds with varying multidrug transporter inhibitory activities. It is particularly intriguing that in at least a few cases, the shift of a bond by one position on an aromatic ring can substantially diminish the activity of some of the most potent inhibitors, suggjesting that there are very specific structural requirements for binding and inhibition. The availability of extensive structural information on both active and inactive analogs will provide a high quality analysis of the effect of various structural variations upon activity.

Many of these inhibitors are highly flexible, making it impractical to perform conventional "2D" QSAR analysis. However, recent techniques have been developed that permit classification of compounds by 3D geometry, and decomposition of activities into various "molecular field" effects. The DISCO (Tripos) and CoMFA (Tripos) software was used for these analyses. Thus, the goal of this analysis was to determine those structural features of the various inhibitors that are most effective in enhancing binding specificity, with emphasis on the three-dimensional or "topological" relationship amongst critical pharmacophores.

As stated earlier, the most active inhibitors fall into several chemically distinct classes suggesting that there may be multiple binding modes, with different chemical structures binding to partially or completely distinct sites within the efflux protein. However, through DISCO analysis of the structure-activity patterns, it is feasible to cluster compounds that bind in a similar mode, and distinguish between clusters that bind in distinctly differing manners (Martin et al., 1993). Using this strategy, it is possible to evaluate the probability of the various chemical classes binding in physically distinct modes. It should be noted that, while there are differing "core" chemical structures, the similarity of some of the "external" moieties suggests that there may also be similarities in the three-dimensional topologies.

INF 55 and INF 271 were used as a pharmacophore model for predicting further analogs with higher activity, because the inventors' initial data indicated that these two inhibitors are both highly effective inhibitors, and appear to bind in modes for which the development of resistance is nearly minimal. The pharmacophore models for these and the inventors' other high activity inhibitors are then be used as guidance in the synthetic strategies outlined schematically below.

The present section, therefore provides details of conventional chemical synthesis strategies in the development of second generation inhibitor analogs for both scientific and economic reasons. At this stage, the inventors have several lead compounds that will require somewhat differing synthetic strategies for analog development. These lead compounds fall into three broad classes of indoles, ureas and aromatic amides. The synthetic strategies in each of these class is discussed in the present section.

a. Indoles

The initial screening process identified a series of nitroindole derivatives. The most potent of these are compounds 1–6 whose activity decreases in the order 1>2~3>4~5~6.

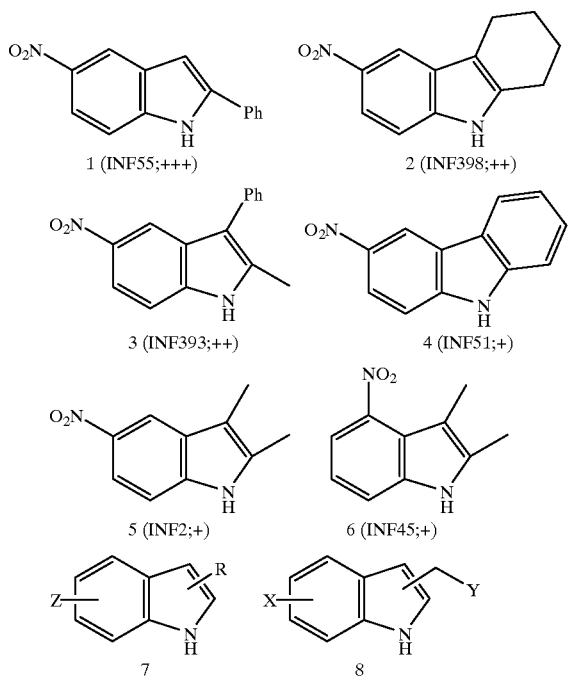

Z = Electron withdrawing group; X = Electron donating group; Y = heteroatomic substituent; R = lipophilic group These six compounds may be broadly summarized as having i) an electron withdrawing nitro group in the benzene ring of the indole moiety, and ii) a lipophilic alkyl or aryl group attached to position 2- or 3- or both of the heterocyclic ring. A further series of indoles with either an electron donating group on the benzene ring and/or a polar heteroatomic based side chain on the heterocyclic ring were considerably less active or even inactive. All of the active indoles have a free indole NH group. Thus, in this series of compounds it would seem most appropriate to undertake a systematic study of rational analogs of the general class represented by formula (7). The synthesis proceeds in a stepwise fashion. Firstly, a further series of 2 and 3-alkyl or aryl indole derivatives all retaining the 5-nitro substituent are synthesized. Subsequentlyv with the optimum alkyl group and location, it is possible to systematically vary the nature and position of the electron withdrawing group.

i. Optimization of the Lipophilic Stibstituents

Judicious combination of structures 1–4 suggests that compounds 9 and 10 should have a high priority for investigation. Neither 9 nor 10 are known compounds but the corresponding derivatives in which the nitro group is replaced by a proton are both known, and have been prepared by the Fischer indole synthesis (Robinson, 1982; Kulagowski et al., 1985; Katritzky and Wango 1988). This gives the inventors a high degree of confidence that both 9 and 10 will be available in one step by Fischer indole reaction of 4-nitrophenylhydrazine with α- and β-tetralone, respectively (Schemes 1 and 2). All of these starting materials are available commercially. The inventors expect that 11 will be a minor product in the synthesis of 10; it will be readily separated from 10 chromatographically, easily distinguished by routine NMR spectroscopy and, of course, screen for activity.

Scheme 1 - the synthesis of compound 9 using a one step Fischer indole reaction of 4-nitrophenylhydrazine with α-tetralone.
Scheme 2 - the synthesis of compounds 10 and 11 using a one step Fischer indole reaction of 4-nitrophenylhydazine with β-tetralone.

SCHEME 1

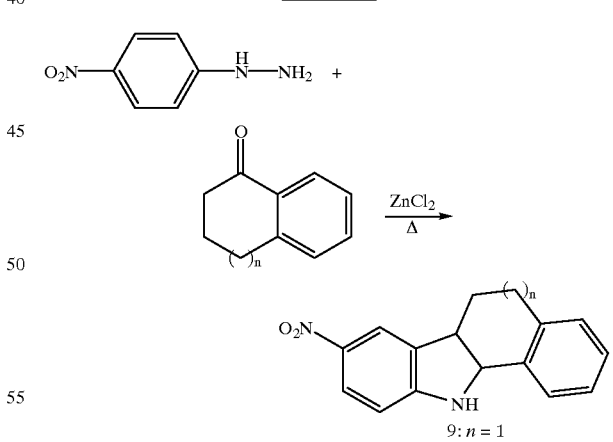

SCHEME 2

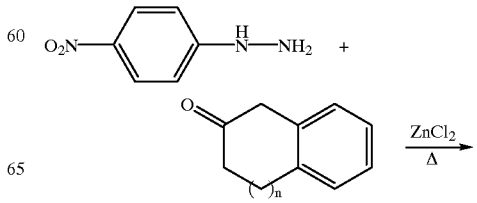

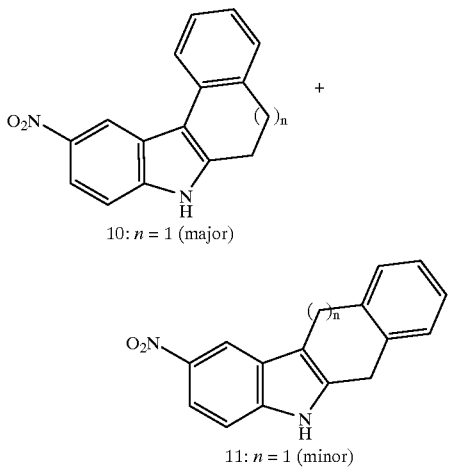

10: n = 1 (major)

11: n = 1 (minor)

It is likely that the phenyl and indole ring in both compound 1 and compound 3 adopt a non-planar conformation for example as shown in compound 13 to minimize steric interactions. If this is indeed the case and if the major conformation is the bound one, models 10 and 11 will be less than ideal as they will hold the two aryl groups close to coplanar. In order to test for this possibility higher homologs (compounds 14–17) of compound 10 and compound 11 are synthesized, again by the Fischer indole synthesis replacing α- and β-tetralones by the corresponding, readily available benzocyclohepotanones and benzocyclooctanones. In this series, as n increases from 1 to 2 to 3 the torsion angle between the two ringis will increase enabling probing of the optimal conformation for binding. The maximum torsion angle (90°) will be best probed via an open chain system such as in compound 18. Again this system is accessible by Fischer indole synthesis, using 2-methylpropiophenone as the ketone component. In addition to this series of constrained 2- and 3-phenyl indole analogs, aliphatic substituents at positions 2 and 3- are sufficient may also be useful; indeed the activity of compound 2 and compound 5 suggests that this may be the case. Such a series of compounds in which the bulk of the alkyl groups is systematically increased also is readily accessible by the Fischer indole synthesis. For example the regiosiomers 19 and 20 are prepared by condensation of 4-nitrophenylhydrazine with pinacolone (tert-butyl methyl ketone) and 2-tert-butylacetaldehyde, respectively.

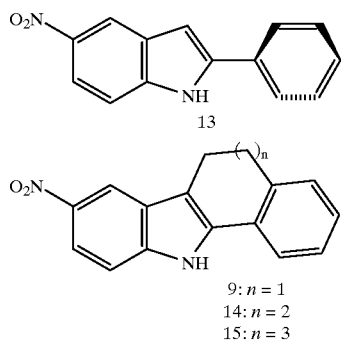

13

9: n = 1
14: n = 2
15: n = 3

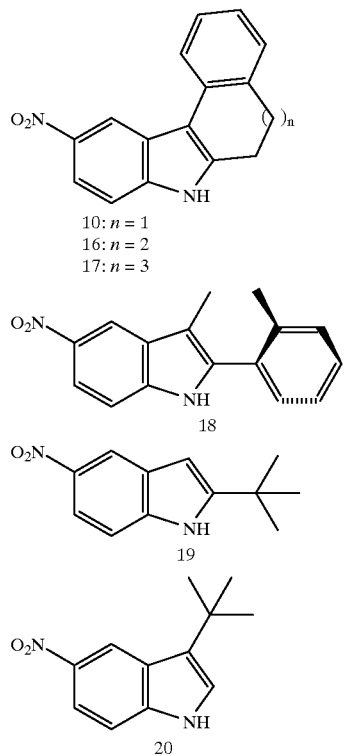

10: n = 1
16: n = 2
17: n = 3

18

19

20

The preparation of each of the above 4-nitroindoles is extremely straightforward and takes place in a single step from 4-nitrophenylhydrazine and a simple ketone. Moreover most of the ketones required are commercially available. Those which are not available commercially are all known compounds for which short, simple preparations are described in the literature. Thus, one of skill in the art will be able to prepare and purify these compounds in sufficient quantity for screening. From these compounds, it is then expected that further alkyl and aryl combinations may be assayed, subsequent to the initial phase.

ii. Location and Nature of the Eectron Withdrawing Group

Having established the optimum combination of alkyl and or aryl groups at the 2-and 3- positions, the best location for the polar group in the benzene ring is determined. This involves a relatively straightforward process, since, in addition to p-nitrophenylhydrazine already employed for the 5-nitro derivatives, o- and m-nitrophenyl hydrazine are commercially available compounds. The syntheses are illustrated in Schemes 3 and 4 with acetophenone as an exemplary ketone, as this will lead to regioisomers of the 2-phenyl-5-nitro compound (compound 1) which was the most active inhibitor from the initial phase of the investigations. However, it is understood that the ketone leading to the optimum selection of hydrophobic groups, as determined from the synthesis in Schemes 1 and 2 above, will be employed in practice in these routine indole syntheses.

With m-nitrophenylhydrazine the synthesis leads to a mixture of the 4- and 6-nitroindoles i.e., compound 21 and i.e., compound 22, respectively (scheme 3). These compounds are separated using standard chromatographic techniques. Subsequent NMR spectroscopy allows the designation of the appropriate structures to the separated compounds. The 7 nitroindole derivative compound 23 is prepared using o-nitrophenylhydrazine as shown in scheme 4.

Scheme 3-synthesis of compounds 21 and 22 using m-nitrophenylhydrazine.
Scheme 4-synthesis of compound 23 using o-nitrophenylhydrazine.

SCHEME 3

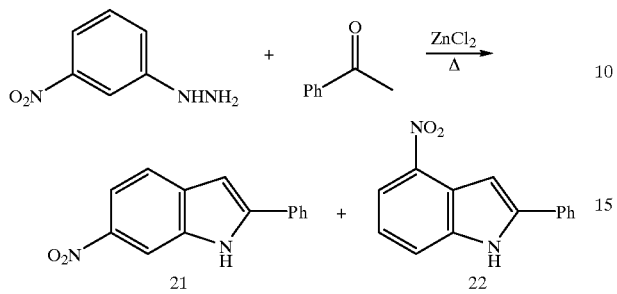

SCHEME 4

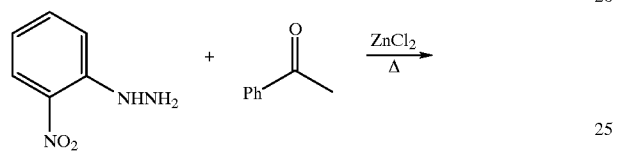

Finally, the inventors turned to the nature of the electron withdrawing group. The lead compounds for this synthesis is one which presents the optimum inhibitory activity from the compounds of lipophilic groups in the heterocyclic ring and for the optimum location in the benzene ring both as determined above. The following provides an illustration of the chemistry for the synthesis of 2-phenylindole with an electron withdrawing group in the 5-position, as in the lead compound 1. Likewise, any other regioisomer that has proves optimal inhibitory activity as described herein may be derivatized as outlined in Schemes 3 and 4.

Alternatively wherever the appropriately substituted hydrazine is commercially available the inventors subject it to the Fischer indole reaction. This was the case with 4-fluor and 4-methylsulfonyl hydrazine (scheme 5). The inventors note that 2- and 3-fluorophenylhydrazine also are commercial, which means that the regioisomeric indoles will be available with a minimum of effort should they be required.

Scheme 5-synthesis of compounds 24 and 25 from 4-fluoro- and 4-methylsulfonyl hydrazine

SCHEME 5

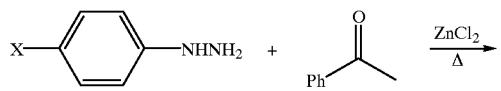

24: X = F
25: X = SO$_2$Me

In some instances, it will prove convenient to synthesize the hydrazone necessary for the Fischer indole reaction from the corresponding substituted aniline derivative. For example this approach may be convenient for the trifluoromethyl substituted series (scheme 6) because o-, m-, and p-trifluoromethylaniline are all readily commercially available.

Similarly, the same reaction format may be used to prepare 2-phenyl 5-iodoindole (or its regioisomers) which will subsequently be benzylated on the indole nitrogen to give the derivative compound 27 (scheme 7).

Scheme 6-synthesis of compound 26.

SCHEME 6

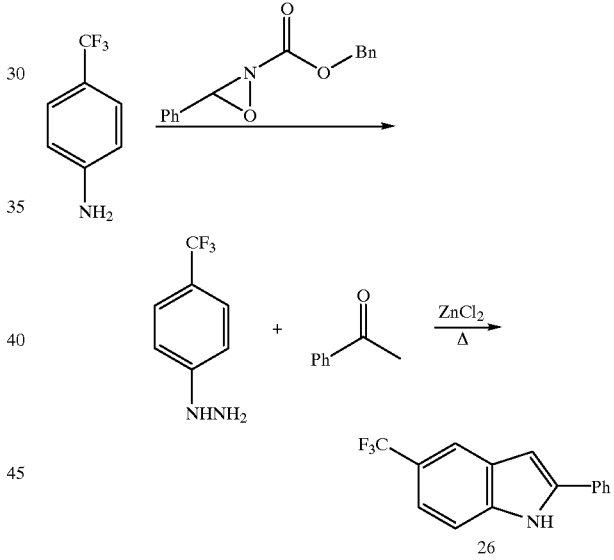

SCHEME 7

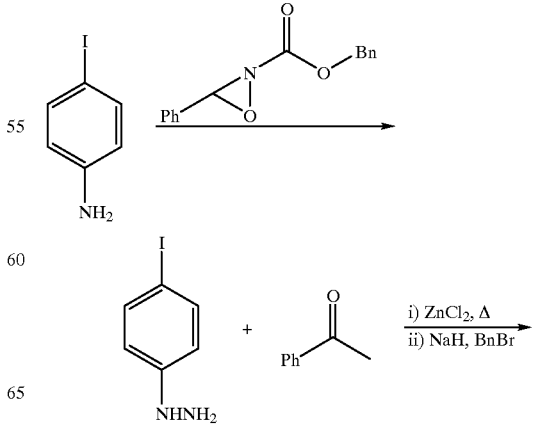

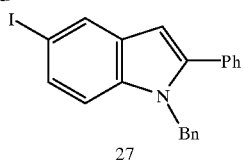

Compound 27 may be transmetallated with tert-butyllithium to give the 5-litho derivative compound 28 which in turn will serve for the introduction of carboxylic (compound 29), sulfonic (compound 30), and phosphonic acid (compound 31) derivatives. Each of these couplings will require a final deprotection of the N-benzyl indole by hydrogenolysis (scheme 8).

to capture a second amine (scheme 9). Numerous or(ganic synthesis protocols are available for this type of reaction.

One common factor in the lead compounds 32–34 is the presence of at least one apolar aromatic substituent, i.e., 4-chlorophenyl in compound 32; 2-naphthyl in compound 33; and 3,4-dichlorophenyl in compound 34. The commercial availability of 4-chlorophenyl isocyanate (compound 35) makes it a suitable candidate to be selected as the starting point for the semi-systematic approach to optimization. Thus, compound 35 is condensed with a wide selection of commercial primary aromatic and aliphatic amines to give the ureas such as compound 36 (scheme 10). The amines R'—NH$_2$ may be selected to probe the essential requirements of the "right hand side" group (R') of the target ureas. Thus it can be determined whether an aryl or alkyl

SCHEME 8

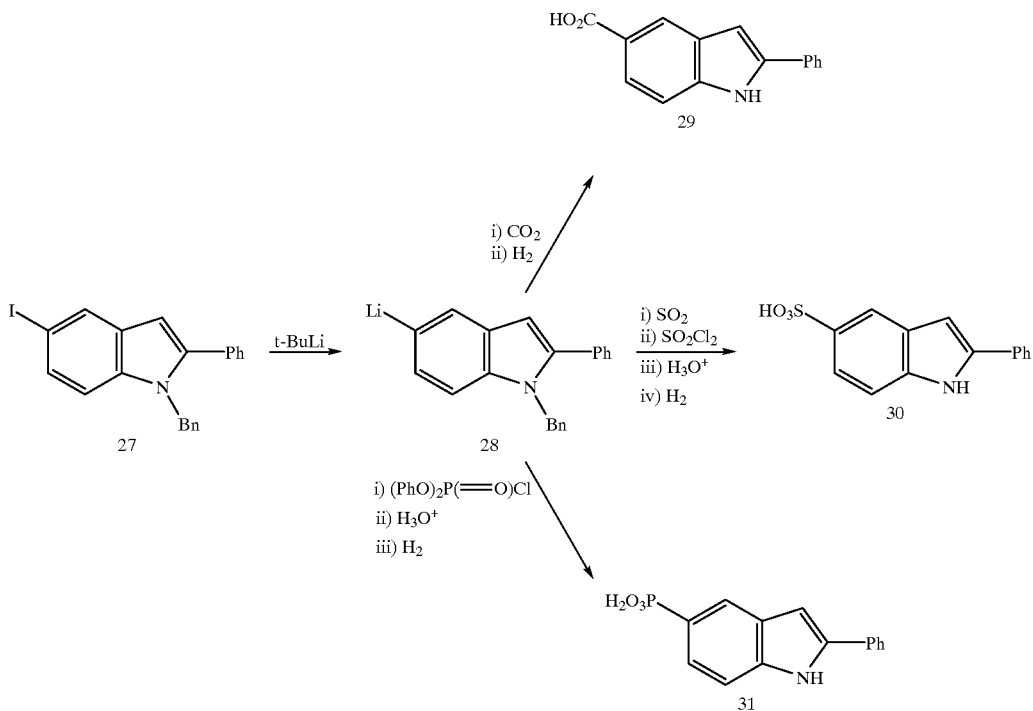

b. Urea Compounds

In the initial screening the inventors isolated three urea compounds (32–34) having high inhibitory activity, but with considerable structural variation. The optimization of these urea leads is described in detail herein below.

The chemistry of ureas is relatively straightforward and the potential for such compounds in medicinal chemistry is very well established. Nowhere is this better highlighted than with the extremely successful, urea based-protease inhibitors introduced in the last few years for the treatment of HIV. The urea-based protease inhibitory compounds are considerably more complex than the structures envisaged here, yet the chemistry of urea synthesis is such that they may be produced commercially on a very large scale. The most straightforward synthesis of unsymmetric ureas involves the condensation of a first primary amine with phosgene to give an isocyanate, which is subsequently used group is preferred and if electron-donating or electron withdrawing functional groups are advantageous and, if so, at what site.

32(INF 377)

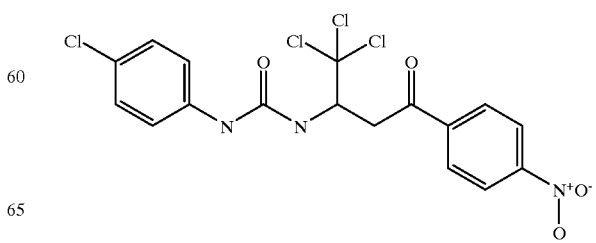

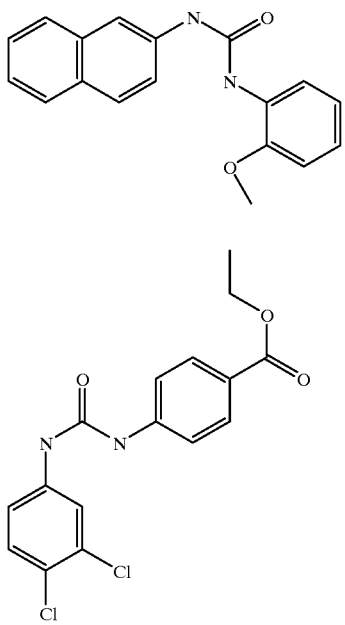

33(INF 271)

34(INF 342)

Scheme 9-synthesis of unsymmetric ureas.

SCHEME 9

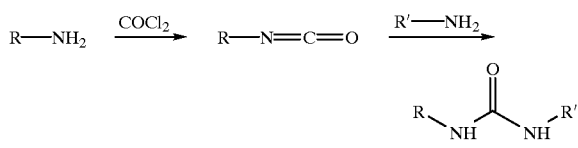

Scheme 10-conversion of 4-chlorophenyl isocyanate to corresponding urea.

SCHEME 10

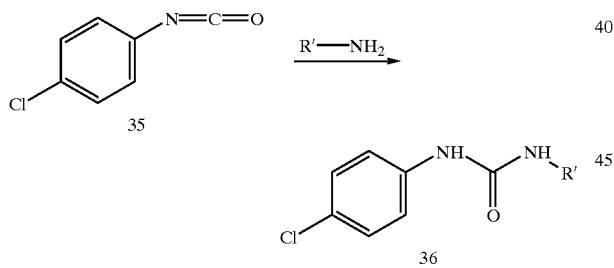

Scheme 11-generation of compound 40 by the condensation of compound 38 with compound 39.

SCHEME 11

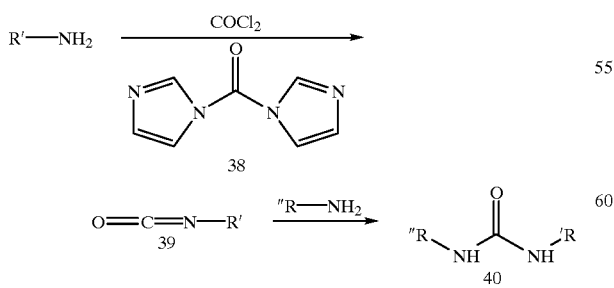

Once an optimal R' group is located for the "right hand side" of the molecule its precursor amine R'—NH, (compound 37) is converted to the corresponding isocyanate, compound 39, which is then be condensed with the same selection of primary aromatic and aliphatic amines, now as R"—NH$_2$, to probe the optimal requirements for the left hand side group (R") in compound 40 (Scheme 11). Depending on the functionality present in the optimal amine R'—NH (compound 37) it can be converted to an isocyanate compound 39 with phosgene or with carbonyl imidazolide (compound 38). Phosgene is used for rapidity and ease of purification when R' is a simple aliphatic or aromatic amine devoid of other nucleophilic centers, whereas its milder, more discriminating analog 38 (Staab and Benz, 1961) is employed with more sensitive R' groups.

In this manner, for a purchase of 4-chlorophenylisocyanate (compound 35) and fifty commercial primary amines, it is possible to synthesize an initial group of fifty ureas (36). Taking the optimal R' group (compound 37) from this selection, converting it to the isocyanate 39, and then condensing with the same fifty amines will yield a second generation series of fifty ureas 40 from which an advanced lead urea compound may be selected and the more precise requirements for both R' and R" determined.

c. 2,5-Disubstituted Pyrimidine-4,6-diones

The most active lead compound in this category was the thiouracil derivative compound 41. A more general structure is represented by the formula compound 42. In order to probe the requirements of the pharmacophore in terms of the two hydrophobic substituent groups, a diverse range of compounds 42 are synthesized in which R and R' are systematically varied. The symmetry inherent in compound 42 and its immediate precursor compound 43 suggest that these compounds will be most readily accessed by a common variant on the Principal Synthesis of pyrimidines. This very well established chemistry is extensively documented in a recent (1994) encyclopedic compilation of the pyrimidine literature (Brown, 1994).

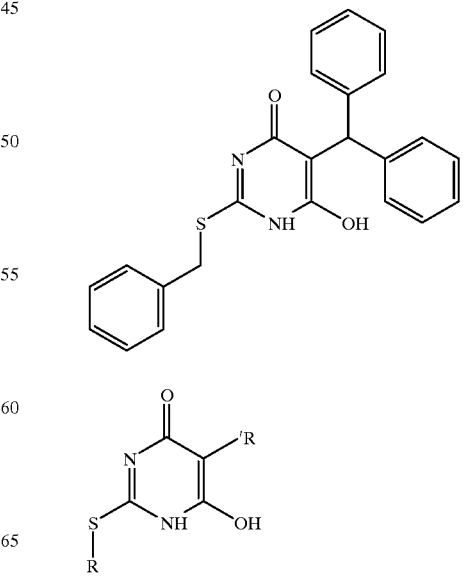

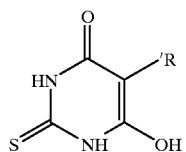

43

SCHEME 13

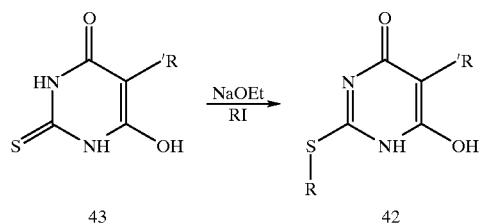

Thus, as indicated in Scheme 12, a range of diethyl alkylmalonate esters 44 may be condensed with thiourea in the presence of sodium ethoxide to give compound 43. This variant on the Principal Synthesis is very well established for all classes of alkyl group (R') and numerous examples are given in the recent review (Brown, 1994). When R' is a primary or secondary alkyl group, the malonate 44 will be obtained routinely by alkylations of diethyl malonate (compound 45) as indicated in scheme 12. When R' is tertiary alkyl, aryl, or vinyl the malonate 44 will be best accessed by condensation of the appropriate ester 46 with ethyl chloroformate, again as indicated in scheme 12.

With 43 in hand, it is possible to turn to the elaboration of analogs of 41. Here, when the desired alkyl group R is a simple primary or secondary alkyld 43 will be alkylated in a straightforward manner with the appropriate alkyl halide and base (Scheme 13). Again there are many examples of such processes in the pyrimidine literature (Brown, 1994). Neither alkylation on nitrogen, nor competing alkylation at either of the two oxygen atoms is reported to be problematic owing to the very high nucleophilicity of such molecules on sulfur (Brown, 1994).

Heating 42 in the presence of an excess of tertiary thiol or arene thiol will enable displacement of methanethiol and the formation of derivatives 47 and 48, which cannot be prepared by the direct alkylation route (scheme 14). The displacement of thiols from pyrimidines in such nucleophilic substitution reactions is well known to those of skill in the art (Brown, 1994).

SCHEME 14

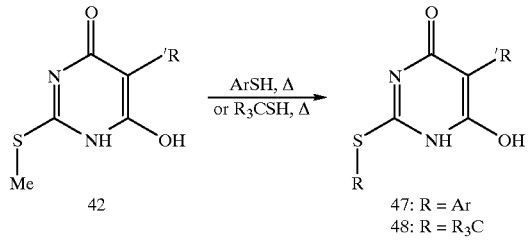

It will be of interest to replace the sulfur atom in 42 with an oxygen or a nitrogen atom as in formulae 49 and 50. This will again be readily achieved through the aegis of 42 (R=Me) and treatment with excess alcohol or base as appropriate (Scheme 15) (Brown, 1994). Certainly, it is more usual in pyrimidine chemistry to make use of chloride as leaving group in such nucleophilic displacements. The requisite chlorides are in turn prepared from the pyrimidone by treatment with $POCl_3$, or related substance. Unfortunately, this is not an option here as any treatment of the 2-oxo-analog of 42 with $POCl_3$ will lead to the preferential introduction of chlorine at the 4- and 6-positions (Brown, 1994). Thus, the chemistry advanced in Schemes 14

SCHEME 12

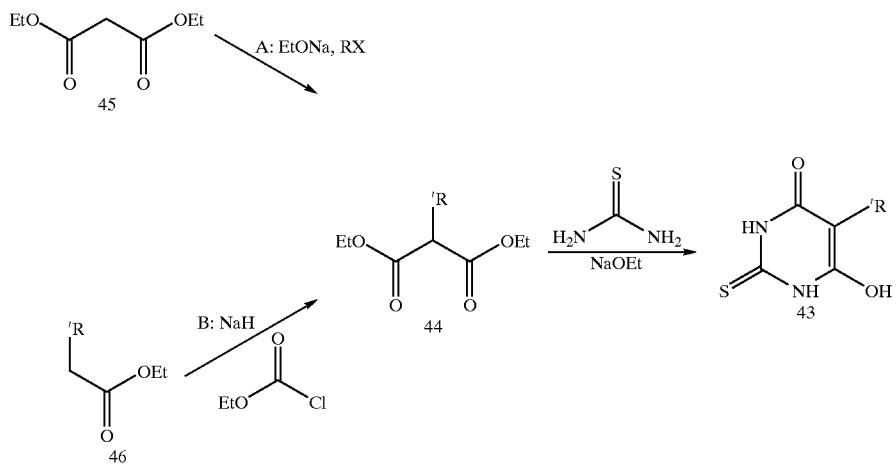

and 15 is designed with the dual objective of i) minimizing effort in the laboratory by taking maximum advantage of the readily available 42 and 43 and ii) overcoming the need for a circuitous route for the selective introduction of chlorine at C2.

SCHEME 15

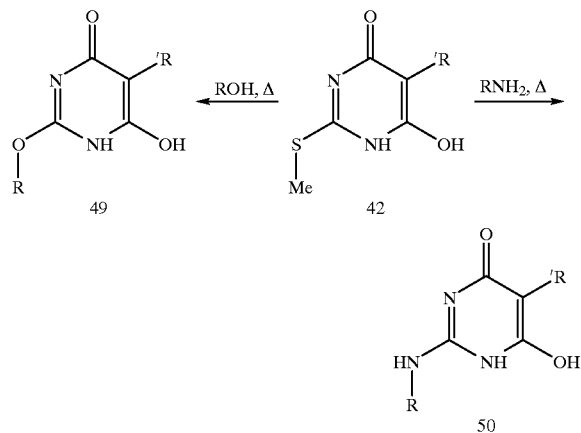

Finally, it will be important to determine whether or not it is necessary to have a heteroatom at C2 at all. Analogs with all carbon side chains at position 2 may be prepared by another known variant of the Principal Synthesis (Brown, 1994) in which amidines are condensed with the malonate esters 44, as shown in Scheme 16.

SCHEME 16

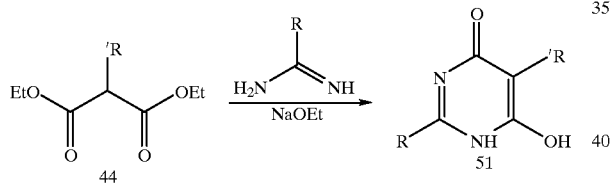

In synthesizing these analogs of 41 the inventors reason that the most efficient approach will be to initially prepare and screen a broad range of compounds 42 with good diversity in the groups R and R'. Once the better combinations of R and R' are identified the inventors will then target the synthesis of a more limited range of the synthetically slightly more elaborate derivatives 47–51.

d. Aromatic Amides

The preparation of aromatic amides related to INF 240 is expected to be straightforward. Thus, for example, it will be well within the skill of one in the art to convert ethyl aminobenzoate 52 (scheme 17), whose ortho, meta- and para-isomers are all commercially available to it tert-butyloxycarbonyl derivative 53. Controlled reduction at −78° C. with diisobutylaluminum hydride (DIBAL-H) will then provide the aldehyde 54 (Jurczak et al., 1989) Wittig olefination will subsequently afford 55. Conditions are available for the preferential formation of both cis- and trans-alkenes by Wittig and related olefination reactions, making both stereoisomers about the double bond readily available (Maryanoff and Reitz, 1989; Vedejs and Peterson, 1994). Treatment of 55 with trifluoracetic acid will cleave the carbonate giving 56, which will then be coupled to an acyl chloride giving the final product 57. A further variation on this straightforward scheme involves catalytic hydrogenation of 55, giving 58 which will then be converted through 59 to 60, the saturated analog of 57. An enormous variety of acid chlorides are commercially available which will permit extensive investigation of the righlt-hand side of the molecule. Similarly, a considerable number of Wittig reagents are commercially available and many others are readily prepared by standard protocols from the corresponding alkyl halides. Thus it is expected that this reaction scheme will provide access to a broad cross-section of differentially substituted aromatic amides.

SCHEME 17

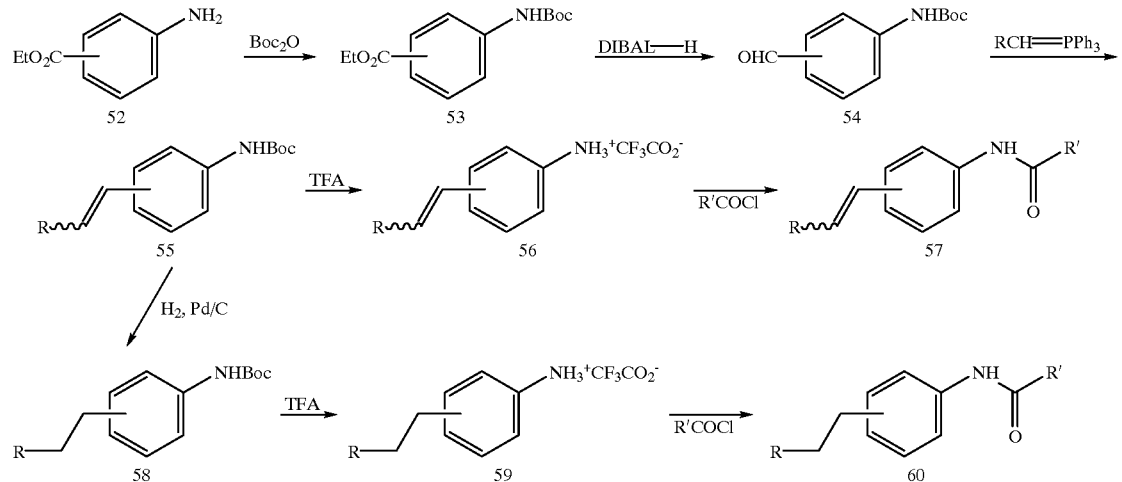

4. Screening

In certain embodiments, the present invention concerns a method for identifying inhibitors of multidrug transporter proteins in bacteria. More particularly, the bacteria are Gram positive bacteria. The methods also concern identifying inhibitors of multidrug transporters of fungal pathogens. The multidrug transporter protein may be any protein that is involved with the efflux of antibacterial agents from a bacterial cell thereby contributing to drug resistance in the particular bacteria. Examples of bacterial infections that may be treated by the inhibitors include but are not limited to those mediated by *S. aureus, S. pneumoniae, B. subtilis E. faecalis, S. epidermidis, M. smegmatis, M. tuberculosis*, and *S. pyogenes*. Fungal infection also may be treated by the inhibitors of the present invention. Such fungal infections may results from pathogens such as *Candida albicans* and other Candida species, as well as *Cryptococcus neoformans, Blastomyces dermatitidis, Histoplasma capsulatum, Torulopis glabrata, Coccidioides immitis, Paracoccidioicdes braziliensis* and Aspergillis. The present invention thus provides methods of identifying inhibitors of multidrug transport proteins such as NorA, Bmr, Blt, Bmr3, PmrA, LmrP and LmrA. It is contemplated that this screening technique will prove useful in the general identification of any compound that will inhibit the efflux of fluoroquinolones in multidrug resistant bacteria (or fungi) and therefore potentiate the effects of the fluoroquinolones in the cells.

Useful compounds in this regard will not be limited to those mentioned above. The active compounds may include fragments or parts of naturally-occurring compounds or may be only found as active combinations of known compounds which are otherwise inactive. However, prior to testing of such compounds in humans or animal models, it may be necessary to test a variety of candidates to determine which have potential.

Accordingly, in screening assays to identify pharmaceutical agents which inhibit multidrug transporters in bacteria and fungi, it is proposed that compounds isolated from natural sources, such as animals, bacteria, fungi, plant sources, including leaves and bark, and marine samples may be assayed as candidates for the presence of potentially useful pharmaceutical agents.

On the other hands one may simply acquire, from various commercial sources, small molecule libraries that are believed to meet the basic criteria for useful drugs in an effort to "brute force" the identification of useful compounds. Screening of such libraries, including combinatorially generated libraries, is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

One library for the compounds identified in the present invention is DiverSet™ (ChemBridge Corp., Glenview, Ill.) The screening of this library consisting of 9.600 compounds, has been completed. The chemical library was screened for compounds effective, at concentrations of 20 µg/ml or less, in reversing the resistance of a specially created *B. subtilis* strain NA to the NorA substrate ethidium bromide. Although the present invention employed NorA as the multidrug transporter in the screening assays it will be understood by one of skill in the art that the compounds identified herein will likely have applicability to other multidrug transporters.

In these embodiments, the present invention is directed to a method for determining the ability of a candidate substance to inhibitors of NorA activity comprising generally including the steps of:

(a) providing a cell expressing only a single functional multidrug transporter, said transporter being Nor A;

(b) contacting said cell with a transportable element in the presence of a candidate inhibitor substance; and (c) comparing the transport of said element by said cell with the transport of said element in the absence of said candidate inhibitor substance.

To identify a candidate substance as being capable of inhibiting NorA activity, one would measure or determine the transport of the transportable substance (e.g., ethidium bromide) by a cell that expresses NorA, in the absence of the added candidate substance. One would then add the candidate substance to the cell and re-determine the efflux of ethidium bromide in the presence of the candidate substance. A candidate substance which reduces the transport of the ethidium bromide relative to the transport in its absence is indicative of a candidate substance with inhibitor capability. Although the present section discusses ethidium bromide as a transportable element, it is understood that these assays may also be performed using any fluoroquinolone whose effect may be monitored by bacteriotoxicity or fungicidal assays.

The candidate screening assay is quite simple to set up and perform. Thus, after obtaining a suitable test cell that has an active multidrug transporter, one will admix a candidate substance in the presence of a transportable substance with the cell, under conditions which would allow the uptake of the transportable substance, for example, ethidium bromide, an antibiotic fluoroquinolone and the like. The inhibition of the transporter can thus be measured by monitoring, for example growth.

In an exemplary assay, in order to identify a candidate substance as an inhibitor of NorA, the *B. subtilis* strain NA may be used. Cells in a logarithmic phase of growth are diluted to an OD600 of e.g, 0.002 and incubated with an effective amount of a candidate substance in the presence of ethidium bromide, fluoroquinolone and the like (e.g., final concentration ¼ MIC ethidium bromide). The cells are transferred to a humidified chamber at optimal growth conditions for an appropriate period of time (e. a, 37° C. for 5 hours) and subsequently examined for growth. Potential inhibitors of transport may be identified as those compounds that increase the bactericidal effect of the ethidium bromide, fluoroquinolone and the like.

"Effective amounts", in certain circumstances, are those amounts effective at reproducibly increasing the bacteriostatic effect of the ethidium bromide or fluoroquinolone in a multidrug resistant bacterial cell in comparison to the level of bactericidal activity of the ethidium bromide or fluoroquintolone in the absence of the candidate substance. Compounds that achieve significant appropriate changes in bactericidal activity of the fluoroquinolone will be used. Thus, a battery of compounds may be screened in vitro to identify other agents for use in the present invention. Tlhe amounts of inhibitors useful in this context may be determined by those of skill in the art and may vary from about 10 ng/ml to about 100 µg/ml. Thus it is contemplated that concentration ranges between these concentrations will be useful including but not limited to 20 ng/ml; 40 ng/ml; 60 ng/ml; 80 ng/ml; 100 ng/ml; 120 ng/ml; 140 ng/ml, 160 ng/ml; 180 ng/ml, 200 ng/ml, 350 ng/ml, 400 ng/ml, 450 ng/ml, 500 ng/ml, 550 ng/ml, 600 ng/ml, 650 ng/ml, 700 ng/ml, 750 ng/ml, 800 ng/ml 900 ng/ml, 1 µg/ml, 5 µg/ml, 10 µg/ml, 15 µg/ml, 20 µg/ml, 25 µg/ml, 30 µg/ml, 35 µg/ml, 40 µg/ml, 45 µg/ml, 50 µg/ml, 55 µg/ml, 60 µg/ml, 65 µg/ml, 70 µg/ml, 75 µg/ml, 80 µg/ml, 85 µg/ml, 90 µg/ml, and 100 µ/ml A significant increase in bactericidal (or fungicidal) activity, e.g, as measured using growth curve analysis are represented by a reduction in bacterial (or fungal) growth of at least about 30%–40%, and most preferably, by decreases of at least about 50%, with higher values of course being possible. Bacterial and fungal growth assays are well known in the art. Therefore, if a candidate substance exhibited multidrug resistance inhibition in this type of study, it would likely be a suitable compound for use in the present invention.

Quantitative in vitro testing of the inhibitor is not a requirement of the invention as it is generally envisioned that the agents will often be selected on the basis of their known properties or by structural and/or functional comparison to those agents already demonstrated to be effective. Therefore, the effective amounts will often be those mounts proposed to be safe for administration to animals in another context, for example, as disclosed herein. There is considerable information available on the use and doses of chemotherapeutic agents alone. which information may now be employed with the present invention.

5. Fluoroquinolones

The therapeutic class of compounds known as the fluoroquinolones is widely known and used in antibacterial treatments (U.S. Pat. No. 4,448,962; DE 3,142,854, EP 206283; U.S. Pat. No. 4,499,091; U.S. Pat. No. 4,704,459; U.S. Pat. No. 4,795,751; U.S. Pat. No. 4,668,784; U.S. Pat. No. 5,532,239 each specifically incorporated herein by reference). Particularly preferred fluoroquiniolonies for use in combination with the multidrug transport inhibitors of the present invention include but are not limited to pefloxacin, norfloxacin, ciprofloxacin, ofloxacin, sparfloxacin, grepafloxaci, Bay 12-8039, trovafloxacin, DU6859a, sarafloxacin, LB20304, levofloxacin, enoxacin, fleroxacin, lomefloxacin, temofloxacin, amifloxacin, tosufloxacin, flumequine, ruflxacin, clinafloxacin and the like. The following section describes treatment regimens using certain fluoroquinolone, these examples merely provide an approximation of the concentrations and formulations of fluoroquinolones that may be used and are not intended to be limiting in any way.

Levofloxacin is a commercially available fluoroquinolone sold under the name Levaquin™ (Ortho-McNeil). It is a synthetic broad spectrum antibacterial agent that may be formulated for intravenous administration or for oral administration. Chemically it is a chiral fluorinated carboxyquinolone that is the S-enantiomer of the drug substance ofloxacin. Levaquin™ is readily available in single use injection as well as appropriately configured solutions in premix flexible containers.

Following a single 60 minute intravenous infusion of 500 mg of levofloxacin to healthy volunteers the peak plasma concentration attained is 6.2 $\mu$g/ml. The plasma concentration profile of the levofloxacin after i.v. administration is similar and comparable in extent of exposure to that observed for levofloxacin tablets when an equal (mg/mg) dose is administered. Thus, the oral and i.v. routes of administration can be considered interchangeable.

Levofloxacin has been shown to be active against Gram negative and Gram positive bacteria. Examples of Gram positive bacteria that levofloxacin has been shown to be useful against include *E. faecalis*, *S. aureus*, *S. pneumoniae*, *S. pyogens*, *C. perfringens*, *S. epidermidis*, Streptococcus (Group C/F), Streptococcus (Group G), *Staphylococcus saprophyticus* and *Streptococcus agalactiae*. Gram negative bacteria shown to be inhibited by levofloxacin include *E. cloacae, E. coil, H. influenzae, H parainfluenzae, K. pneumoniae, L. pneumophila, M. catarrhalis, P. mirabilis, P. aeruginosa, C. pneumoniae, M. pneumoniae, A. anitratus, A. baumannii, A. calcoaceticus, A. lwoffii, B. pertussis, C. diversus, C. freundii, E. aerogenes, E. agglomerans, K. oxytoca, M. morganii, P. vulgaris, P. rettaeri, P. stuartii, P. fluorescens* among others. It is envisioned that the MDT inhibitors identified in the present invention may be used in combination with levofloxacin to inhibit or reduce the growvth of some or all of these organisms.

In particular, levofloxacin has been indicated for the treatment ol individuals with mild, moderate and severe infection caused by strains of the designated microorganisms. Particular indications include acute maxillary sinusitis. acute bacterial exacerbation of bronchitis, acquired pneumonia, uncomplicated skin and skin structure infections, complicated urinary tract infection, and acute pyelonephritis.

The usual dose of Levaquin™ is 500 mg administration by slow infusion over a 60 minute period every 24 hours or as determined by the physician according to the appropriate creatinine clearance. Levaquin™ tablets may be given as 500 mg orally every 24 hours. The skilled artisan is referred to the Physicians Desk Reference, (52nd edition 1998, incorporated herein by reference) for more details on amounts and duration of doses.

Norfloxacin is sold under the clinical name Chibroxin™ (Merck & Co.) as an opthalmic solution and as Noroxin™ (Merck & Co.) tablets for oral administration. In fasting healthy volunteers at least 30–40% of the oral dose of Noroxin is absorbed. Absorption is rapid following single doses of 200 mg 400 mg and 800 mg. At the respective single doses, the mean peak serum and plasma concentrations of 0.8, 1.5 and 2.4 $\mu$g/ml are attained approximately one hour after dosing.

Norfloxacin has been shown to be active against most strains of *Staphylococcus aureus, Staphylococcus epidermidis, Staphylococcus warnerii* and *Streptococcus pneumoniae* Gram positive bacteria. Gram-negative bacteria against which Norfloxacin is clinically useful include *Acinetobacter calcoaceticus, Aeromonas hydrophila, Haemophilus influenza, Proteus mirabilis, Pseudomonas aeruginos* and Serratia. Norfloxacin also has been shown to be valuable in vitro against *Bacillus cereus, Entercoccus faecalis* (formerly *Streptococcus faecalis*), *Staphylococcus saprophyticus* (all Gram-positive bacteria) and *Citrobacter diversus, Citrobacter freundii, Edwardsiella tarda, Enterobacter aerogenes, Enterobacter cloacac, Escherichia coli, Hafnia alvei, Haemophilus aegyptius* (Koch-Weeks bacillus), *Klebsiella oxytoca, Klebsiella pneumoniae, Klebsiella rhinoscleromatis, Morganella morganii, Neisseria gonorrhoeae, Proteus vulgaris, Providencia alcalifaciens, Providencica rettgeri, Providencia stuartii, Salmonella typhi, Vibrio cholerae, Vibrio parahemolyticus, Yersinia enterocolitica* (Gram negative bacteria).

Norfloxacin is indicated for the treatment of adults with urinary tract infections, sexually transmitted disease and prostatitis. For more detailed disclosure on the specific microorganisms mediating these infections the skilled artisan is referred to the Physicians Desk Reference, (pp. 607–608; 52nd edition, 1998, incorporated herein by reference). Norfloxacin tablets may be administered in a single dose or multiple doses. the recommended dose is a 400 mg tablet once daily for between about 1 day to about 28 days depending on the nature of the infection. The skilled artisan is referred to the Physicians Desk Reference, (52nd edition, 1998, incorporated herein by reference) for more details on amounts and duration of doses.

Ciprofloxacin is available in opthalmic solution, intravenous injection solution and tablet formulation. Cipro™ is a broad spectrum fluoroquinolone that is available in 100 mg, 250 mg, 500 mg, and 750 mg coated tablets which are rapidly and well absorbed from the gastrointestinal tract after oral administration.

Ciprofloxacin has been shown to be active against most strains of the following microorganisms both in vilro and in clinical infections. Aerobic gram-positive bacteria against which ciprofloxacin is active include *Enteocococcus faecalis, Staphylococcus epidermidis, Staphylococcus saprophyticus, Streptococcus pneumoniae, Streptococcus pyogenes, Staphylococcus aureus*. Ciprofloxacin is clinically bacteriotoxic against various aerobic gram-negative bacteria including *Campylobacter jejuni, Citrobacter diversus, Citrobacter freundii, Enterobacter cloacae, Esherichia coli, Haemophilus influezae, Haemophilus parainfluenzae, Klebsiella pneumoniae, Moraxella catarrhalis, Morganella morganii, Nisserica gonorrhoeae, Proteus mirabilis, Proteus vulgaris, Proivdencia rettgeri, Providencia stuartii, Pseudomonas aeruginosa, Salmonella typhi, Serratica marcensens Shigella boydii, Shigella dysenteriae, Shigella flexneri* and *Shigella sonnei*. Ciprofloxacin exhibits in vitro minimal inhibitory concentrations (MICs) of $\leq 1$ $\mu$g/mL against most ($\geq 90\%$) strains of the following microorganisms; however, the safety and effectiveness of ciprofloxacin in treating clinical infections due to these microorganisms have not been established in adequate and well-controlled clinical trials. These bacteria include *Acinetobacter Iwoffi*, Aeromonacs caviae, Aeromronas caviae, Aeromonas hydrophila, Brucella melitensis, Campylobacter coli, Edwardsilla tarda, Haemophilus ducreyi, Klebsiella oxytoca, Legionella penumophila, Neisseria meningitidis, Neisseria meningitidis, Pasteurella multocida, Salmonellca enteritidis, Vibrio cholerae, Vibrio paraphaemolyticus, Vibrio vulnificus, Yersinia enterocolitica.

Cipro™ is indicated for the treatment of infection such as acute sinusitis, lower respiratory infections, urinary tract infection, acute uncomplicated cystitis in females, chronic bacterial prostatitis, complicated intra-abdominal infections, skin and skin structure infections, bone and bone joint infections, infectious diarrhea, typhoid fever and uncomplicated cervical and urethral gonorrhea. For more detailed disclosure on the specific microorganisms mediating these infections the skilled artisan is referred to the Physicians Desk Reference, (pp. 607–608; 52nd edition, 1998, incorporated herein by reference).

The dose of Cipro™ for acute sinusitis is 500 mg every 12 hours. Lower respiratory infections may be treated with 500 mg every 12 hours. For more severe or complicated infections, a dose of 750 mg may be given every 12 hours. Urinary tract infection may be treated with 250 mg to 500 mg every 12 hours depending on the severity of the infection. Acute uncomplicated cystitis in females usually requires 100 mg every 12 hours. This infection 3 days of treatment may be appropriate whereas 7 to 14 days is recommended for other urinary tract infections. Treatment of chronic bacterial prostatitis uses a regimen of 500 mg every 12 hours.

The adult dose for complicated intra-abdominal infections is a sequential oral therapy in which 500 mg are administered daily. The skilled artisan is referred to the Physicians Desk Reference. (pp. 608; 52nd edition, 1998, incorporated herein by reference) for detailed protocols of such sequential therapy. Skin and skin structure infections, infectious diarrhea, typhoid fever and bone and bone joint infections are generally treated with a daily 500 mg dose, whereas urethral and cervical gonococcal infections may be treated with a single 250 mg dose. The Physicians Desk Reference provides a more detailed protocol of doses, administration time indications and contraindications of this and the other fluoroquinolone described.

Floxin™ is the tradename for the intravenous formulation of otloxacin. It is another broad spectrum, widely prescribed fluoroquinolone. Oral and intravenous administration appears to be similar and comparable in extent of exposure to that observed when an equal (mg/mg) dose is administered. Thus, the oral and i.v. routes of administration can be considered interchangeable.

Floxin™ has been shown to be effective against the following bacteria *S. aureus, S. pneumoniae, S. pyogenes*, as wells as *C. diversus, E. aerogenes, E. coli, H. influenzae, K. pneumonia, N, gonorrhoeae, P. mirabilis* and *P. Auruginosa*. Floxin I.V also has been show to be useful against *Staphylococaus epidermidis, Staphylococcus haemolyticus, Staphyloccus saprophyticus, Acinetobacter calcoaceticus, Aeromonas caviae, Aeromonas hydrophila, Bordetella parapertussis, Bordetella pertussis, Citrobacter freundii, Enterobacter cloacae, Haemophilus ducreyi, Klebsiella oxytoca, Moraxella catarrhalis, Morganella morganii, Proteus vulgaris, Providencia rettgeri, Providencia stuartii, Serratia Marcescens* and *Vibrio parhaemolyticus*.

Floxin™ is indicated in acute bacterial exacerbation of chronic bronchitis, community acquired pneumonia, uncomplicated skin and skin structure infections, acute and uncomplicated urethral and cervical gonorrhea, nongonoccocal urethritis and cervicitis, mixed infections of the urethra and cervix, acute pelvic inflammatory disease, uncomplicated cystitis, complicated urinary tract infections, and prostatitis. For more detailed disclosure on the specific microorganisms mediating these infections the skilled artisan is referred to the Physicians Desk Reference, (pp. 1990–1991; 52nd edition, 1998, incorporated herein by reference)

According to the manufacturers instructions (Ortho-McNeil), Floxin™ I.V. should only be administered by intravenous infusion and may not be used for intramuscular, intrathecal, intra peritoneal or subcutaneous administration. The Floxin™ injection should be administered slowly over a period of not less than 60 minutes. The usual doses of Floxin™ is 200 mg to 400 mg administered by slow infusion every 12 hours tor patients presenting mild to moderate infections and normal renal function. Thus the dosage of Floxin may vary from 400 mg to 600 mg per day and the duration of treatment can be from between 1 day to as much as 6 weeks. For specific details regarding the dosages and duration of administration for particular indications the skilled artisan is referred to page 1993 of the Physicians Desk Reference. (52nd edition, 1998, incorporated herein by reference). Oral formulations of Floxin® also are available and the skilled artisan is referred to page 1997 of the Physicians Desk Reference for additional disclosure regarding dosages and duration of administration.

Penetrex™ is yet another commercially available fluoroquinolone with a broad spectrum specificity. Penetrex™ is the tradename for enoxacin and is available in an oral formulation. Enoxacin is an inhibitor of the bacterial enzyme DNA gyrase and is a bactericidal agent. Enoxacin may be active against pathogens resistant to drugs that act by different mechanisms.

Penetrex™ has been shown to be active against most strains of the following organisms both in vitro and in clinical infections in *Staphylococcus epidermidis* and *Staphylococcus saprophyticus* (Gram-positive aerobes) and *Enterobacter cloacae, Escherichia coli, Klebsiella pneumoniae, Neisseria gonorrhoeae, Proteus mirabilis, Pseudomnonas aeruginosa* (Gram-negative aerobes). In addition, enoxacin exhibits in vitro minimum inhibitory concentrations (MICs) of 2.0 μg/mL or less against most strains of certain other organisms; however, the safety and effectiveness of enoxacin in treating clinical infections due to these organisms have not been established in adequate and well controlled trials, these Gram negative aerobes include *Aeromonas hydrophila, Citrobacter diversus, Citrobacter freundii, Citrobacter koseri, Enterobacter aerogenes, Haemophilus ducreyi, Klebsiella oxyloca, Klebsiella ozaenae, Morganella morganii, Proteus vulgaris, Providencia stuartii, Providencia alcalifaciens, Serratia marcescens, Serratia proteomaculans* (formerly *S. Liquefaciens*)

Penetrex™ is indicated for the treatment of adults presenting sexually transmitted diseases and urinary tract infections. Specific dosing details may be obtained from the Physicians Desk Reference p2379–2380.

Lomefloxacin is available as Mexaquin® in tablet form for oral administration. Mexaquin is available as a film coated tablet containing 400 mg lomefloxacin base. Lomefloxacin is a bactericidal agent with in vitro activity against a wide range of Gram-negative and Gram-positive organisms. The bactericidal action of lomefloxacin results from interference with the activity of the bacterial enzyme DNA gyrase, which is needed for the transcription and replication of bacterial DNA. The minimum bactericidal concentration (MBC) generally does not exceed the minimum inhibitory concentration (MIC) by more than a factor of 2, except for staphylococci, which usually have MBCs 2 to 4 times the MIC.

Lomefloxacin has been shown to be active against most strains of the following organisms both in vitro and in clinical infections: *Staphylococcus saprophyticus* Gram positive bacteria and a longer list of Gram negative bacteria including *Citrobacter diversus, Enterobacter cloacae, Escherichia Klebsiella, pneumoniae coli, Haemophilus influenzae, Moraxella* (*Branhamella*) *catarrhalis, Proteus mirabilis, Pseudomonas aeruginosa* (urinary tract only). Lomefloxacin exhibits in vitro MICs of 2 μg/ml or less against most strains of the following organisms; however, the safety and effectiveness of lomefloxacin in treating clinical infections due to these organisms have not been established in adequate and well-controlled trials. In vitro data is available against *Staphylococcus aureus* (including methicillin-resistanit strains) *Staphylococcus epidermidis* (including methicillin-resistant strains) Gram positive aerobes and various Gram negative bacteria including *Aeromonas hydrophila, Citrobacter freundii, Enterobacter aerogenes, Enterobracter agglomerans, Haemophiltus parainfluenzae, Hafnia alvei, Klebsiella oxytoca, Klebsiella ozaenae, Morganella morganni, Serratia liquefaciens, Proteus vulgaris, Providencia alcalifaciens, Providencia rettgeri* and *Serratia marcesescens.*

Maxaquin™ tablets are indicated for the treatment of adults with mild to moderate infections caused by susceptible strains of microorganisms in conditions such as lower respiratory tract infections and urinary tract infections. Maxaquin™ has been particularly indicated in the prevention and prophylaxis of transrectal prostate biopsy and transurethral surgical procedures. On both instances a 400 mg single dose may be orally administered between 1 to 6 hours prior to the operative procedure. For additional details on administration protocols the skilled artisan is referred to the Physicians Desk Reference pp. 2744–2748.

The fluoroquinolones discussed above are exemplary fluoroquinolones that may be used in combination with the MDT inhibitors of the present invention. It is understood that the MDT inhibitory compositions of the present invention may be used in combination with any fluoroquinolone in order to potentiate the effect of that fluoroquinolone and/or circumvent or prevent resistance to such a drug. Further, it is contemplated that any of the infections listed herein above or any other infection that is treatable by fluoroquinolone administration will be amenable to treatment with the MDT inhibitors of the present invention in combination with fluoroquinolone treatment.

6. Combination Therapy

Bacterial intrinsic and acquired resistance to antibiotics represents a major problem in the clinical management of bacterial infections. This resistance is mediated at least in part due to the proficiency of the multidrug efflux proteins that are now known to be abundant in bacteria. There are numerous antibiotic ajents that would be excellent therapeutic agents in combating bacterial infection but for the their active efflux from the bacterial cells by the action of these MDT proteins. Thus, one of the goals of current chemotherapeutic research is to find ways of improving the efficacy of existing bactericidal compounds against bacterial infection.

One way of achieving such a beneficial therapeutic outcome is to combine traditional antibiotics with agents that inhibit the efflux activity of the multidrug transporter. Such combination antibiotic therapy would be conceptually similar to the already widely used combinations of β-lactam or cephalosporin antibiotics with inhibitors of β-lactamase. In fact. one such combination, augmentin, has become the most frequently prescribed antibiotic preparation in the United States. More particularly, it is a goal of the present invention to improve the efficacy of fluoroquinolone activity. The inventors propose that the clinical use of fluoroquinolones in combination with an inhibitor of multidrug transporters should dramatically improve the clinical efficacy of these antibiotics by both reducing their effective concentration several fold (shifting it well below their practically achievable tissue levels) and preventing the emergence of drug-resistant variants. More specifically the present invention provides combinations of a fluoroquinolone and an inhibitor of multidrug transporter(MDT inhibitor) for combating Gram positive infection. Equally in mycological applications, the MDT inhibitors may be combined with other anti-fungal treatments.

To kill bacterial cells, inhibit bacterial cell growth, or otherwise reverse or reduce the suppressing effect on the emergence of drug-resistant variants bacterial species using, the methods and compositions of the present invention. one would generally contact a "target" cell with an MDT inhibitor and at least one fluoroquinolone. The antifungal applications of the present invention will be similar except that the cells being killed, inhibited or suppressed will be fungal cells. The compositions would be provided in a combined amount effective to kill or inhibit bacterial cell growth. This process may involve contacting the cells with the MDT inhibitor and the fluoroquinolone(s) or other bactericidal factor(s) at the same time. This may be achieved by contacting the cell with a single composition or pharmacological formulation that includes both agents, or by contacting the cell with two distinct compositions or formulations. at the same time, wherein one composition includes the MDT inhibitor and the other includes the fluoroquinolone.

The MDT inhibitor treatment may precede or follow the other fluoroquinolone by intervals ranging from minutes to hours to days. In embodiments where the fluoroquinolone and MDT inhibitor are administered separately, one would generally ensure that a significant period of time did not expire between the time of each delivery, such that the fluoroquinolone and MDT inhibitor would still be able to exert an advantageously combined effect on abrogating the bacterial infection. In Such instances, it is contemplated that one would administer both modalities within about 12–24 hours of each other and, more preferably, within about 6–12 hours of each other, with a delay time of only about 12 hours being most preferred, It may be that in order to sensitize the bacterial cells to the fluoroquinolone treatment. the MDT inhibitol is administered for a sufficient period of time (1, 2 3, 4, 5, 6, 7, 8, 12, 24 hours) prior to the fluoroquinolone treatment. In some situations, it may be desirable to extend the time period for treatment significantly, however, where several days (2, 3, 4, 5, 6 or 7) to several weeks (1,2, 3, 4, 5, 6, 7 or 8) lapse between the respective administrations. Equally it may be necessary to administer multiple doses of the MDT inhibitor in order to sensitize the bacterial cells to the fluoroquinolone treatment.

It also is conceivable that more than one administration of either MDT inhibitor or the fluoroquinolone will be desired. Various combinations may be employed, where the MDT inhibitor is "A" and the fluoroquinolone is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve bacterial cell killing, both agents are delivered to a cell in a combined amount effective to kill the cell and remove the infection.

Agents or factors suitable for use in a combined therapy are any fluoroquinolone chemical compound or treatment method that induces damage when applied to a bacterial cell. More particularly, the present invention uses fluoroquinolone in combination with the MDT inhibitors of the present invention. Such fluoroquinolones include but are not limited to pefloxacin, norfloxacin, ciprofloxacin, ofloxacin, levofloxacin, enoxacin, fleroxacin, lomefloxacin, temofloxacin, amifloxacin, tosufloxacin, flumequine, rufloxacin. clinafloxacin and the like.

In certain embodiments, the MDT inhibitors of the present invention may be used in combination with antifungal agents to combat fungal infection. Such antifungal agents include but are not limited to amphotericin B. flucytosine, ketoconazole, miconazole, itraconazole, fluconazole, griseofluconiazole, clotrimazole, econazole, terconazole. butaconazole, nystatin, haloprogin, loprox, natamycin, undecylenic acid and others.

In treating a bacterial infection according to the invention, one would contact the bacterial cells with a fluoroquinolone agent in addition to the MDT inhibitor. This may be achieved by contacting the bacterial cells with the agent by administering to the subject a therapeutically effective amount of a pharmaceutical composition comprising a fluoroquinolone compound and a therapeutically effective amount of the MDT inhibitor. Similarly, in treating a fungal infection according to the invention, one would contact the fungal cells with an antimycotic agent in addition to the MDT inhibitor. The antifungal or antibacterial agent may be prepared and used as a combined therapeutic composition. or kit, by combining it with a MDT inhibitor, as described above.

The skilled artisan is directed to "the Physicians Desk Reference" 52nd Edition, in order to find detailed specific disclosure regarding particular fluoroquinolonles. Some variation in dosage will necessarily occur depending on the condition of the subject beiln treated. The person responsible for administration will, in any event, determine the appropriate dose for the individual subject. Moreover, for human administration. preparations should meet sterility, pyrogenicity, general safety and purity standards as required by the FDA Office of Biologics standards.

The inventors propose that the regional delivery of MDT inhibitor and/or the fluoroquinolone compositions to patients with Gram positive bacterial infection will be a very efficient method for delivering a therapeutically effective composition to counteract the clinical disease. Alternatively, systemic delivery of MDT inhibitor and/or the fluoroquinolone may be the most appropriate method of achieving therapeutic benefit from the compositions of the present invention. Likewise, the MDT inhibitor and/or antimycotic agent compositions may be administered to patient with fungal infection as a regional delivery, systemic delivery or topical application.

It also should be pointed out that any of the foregoing MDT inhibitors may prove useful by themselves in treating a bacterial or fungal infection. In this regard, reference to chemotherapeutics in combination also should be read as a contemplation that these approaches may be employed separately.

7. Pharmaceutical Administration

Pharmaceutical compositions of the present invention will generally comprise an effective amount of the MDT inhibitor dissolved or dispersed in a pharmaceutically acceptable carrier or aqueous medium. The pharmaceutical composition may further comprise a fluoroquinolone composition.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The MDT inhibitor of thlc present invention will often be formulated for parenteral administration, e.g., formulated for injection via the intravenous, intramuscular. subcutaneous or other such routes, including direct instillation into an infected or diseased site. The preparation of an aqueous composition that contains an MDT inhibitor agent as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection also can be prepared; and the preparations also can be emulsified.

Solutions of the active compounds as free base or pharmacologically acceptable salts can be prepared in water suitably mixed with a surfactant. such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The MDT inhibitor compositions can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylarnine. trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. Formulations are easily administered in a variety of dosage forms, such as the type of injectable solutions described above, but drug release capsules and the like also can be employed.

Suitable pharmaceutical compositions in accordance with the invention will generally include an amount of the MDT inhibitor admixed with an acceptable pharmaceutical diluenit or excipient, such as a sterile aqueous solution, to give a range of final concentrations, depending on the intended use. The techniques of preparation are generally well known in the art as exemplified by Remington's Pharmaceutical Sciences. 16th Ed. Mack Publishing Company, 1980, incorporated herein by reference. It should be appreciated that, for human administration, preparations should meet sterility, pyrogenicity, general safety and purity standards as required by the FDA Office of Biological Standards.

The therapeutically effective doses are readily determinable using an animal model, as shown in the studies detailed herein. Experimental animals bearing bacterial or fungal infection are frequently used to optimize appropriate therapeutic doses prior to translating to a clinical environment. Such models are known to be very reliable in predicting effective anti-bacterial and anti-flungal strategies.

In addition to the compounds formulated for parenteral administration, such as intravenous or intramuscular injection, other pharmaceutically acceptable forms also are contemplated, e.g. tablets or other solids for oral administration, time release capsules, liposomal forms and the like. Other pharmaceutical formulations may also be used, dependent on the condition to be treated.

For oral administration the MDT inhibitors of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The present invention also provides therapeutic kits comprising the MDT inhibitors described herein. Such kits will generally contain, in suitable container means. a pharmaceutically acceptable formulation of at least one MDT inhibitor in accordance with the invention. The kits may also contain other pharmaceutically acceptable formulations, such as those containing antibiotics such as fluoroquinolones; and any one or more of a range of chemotherapeutic drugs.

The kits may have a single container means that contains the MDT inhibitor, with or without any additional components, or they may have distinct container means for each desired agent. Certain preferred kits of the present invention include a MDT inhibitor, packaged in a kit for use in combination with the co-administration of fluoroquinolones. In such kits, the MDT inhibitor and the fluoroquinolone may be pre-complexed, either in a molar equivalent combination, or with one component in excess of the other; or each of the MDT inhibitor and fluoroquinolone components of the kit may be maintained separately within distinct containers prior to administration to a patient. Other preferred kits include any MDT inhibitor of the present invention in combination with a "classic" chemotherapeutic agent. This is exemplary of the considerations that are applicable to the preparation of all such MDT inhibitor kits and kit combinations in general.

When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means.

The container means of the kit will generally include at least one vial, test tube, flask, bottle, syringe or other container means, into which the MDT inhibitor, and any other desired agent, may be placed and, preferably, suitably aliquoted. Where additional components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the MDT inhibitor to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without eparting from the spirit and scope of the invention.

Example 1

CoMFA (3D-QSAR) Analysis for Potential Inhibitors of the Multidrug Transporter NorA The DiverSet™ library of chemical compounds was screened for compounds effective, at concentrations of 20 $\mu$g/ml or less, in reversing the resistance of a specially created *B. subtilis* strain NA to the NorA substrate ethidium bromide. 399 compounds were suggested as potential inhibitors. Of these 399, 54 showed activity at 5 $\mu$g/mL or less, while the others showed moderate to little activity at 10–20 $\mu$g/mL. Three of the most potent compounds are shown below as INF55 with an indole moiety; a urea compound, INF271; and INF240, possessing an aromatic amide functional group. A large number of other compounds in this set could be classified according to these three, and since it is unclear whether NorA has more than one potential binding site, the compounds were subdivided into the indoles (and nitroindoles), the ureas, and the aromatic amides. These three classes of compounds were evaluated using the activity data provided and the CoMFA fields generated to see if a 3D-QSAR relationship was present.

Computational Methods

All of the compounds in the study were initially optimized using MM3, and a conformational search done to find the lowest energy conformer. Subsequently, this lowest energy conformer was then reoptimized (also at MM3), and used as the inventors' initial geometry. The partial atomic charges were generated using AM1 (Dewar et al., 1985) within Sybyl 6.4 (Tripos, Inc., St. Louis, Mo.). The CoMFA analysis was performed using Sybyl 6.4. One of the big concerns for a CoMFA analysis is the choice of superposition. The inventors chose to use DISCO (Martin et al., 1993) to overlay the molecules, which finds common pharmacaphore points within the set of compounds (and their conformers). More than one DISCO model was generally found, and the model with the best fit (overlay) was used for each class of compounds. This overlay of molecules was then used to generate the CoMFA steric and electrostatic fields. Using the CoMFA and activity data, a PLS analysis was performed to check the validity of the model. First cross-validation PLS was run to optimize the number of components and to check the $r^2_{cv}$. For the inventors' analysis the $r^2_{cv}$ value was no lower than 0.42 for any of the inventors' systems. The $r^2$ and F value were then determined with the optimal number of components and with no cross-validation. These values are presented in Table 1 for all of the systems.

Results

Indoles. The nitroindoles and indoles were the first class of compounds analyzed. Initially these two were studied separately. There were only a small number of nitroindoles studied. 13 compounds, resulting in a mediocre model (see Table 1). There were a total of 40 indoles that did not possess a substituent at the nitrogen position that also were modeled resulting in a better model than the nitroindoles. However, the best model (from PLS analysis, Table 1) generated was upon the inclusion of the nitroindoles with the indoles, where the inventors had a total of 49 compounds. This model was then used to evaluate the steric and electrostatic fields for all and used for predicting activities of other indoles. The steric and electrostatic field contour maps generated by CoMFA are shown with INF55 in FIG. 1 and FIG. 2.

TABLE 1

Results from PLS analysis for the Systems Evaluated

| System | Number of Compounds in analysis | $R^2$ | F value | Standard error of estimate | Probe atom |
|---|---|---|---|---|---|
| Nitroindoles | 13 | 0.781 | 39.181 | 0.273 | sp$^3$C(+1) |
| Indoles | 40 | 0.953 | 371.603 | 0.059 | sp$^3$C(+1) |
| Nitroindoles + Indoles | 49 | 0.995 | 1611.971 | 0.034 | sp$^3$C(+1) |
| Ureas | 28 | 0.951 | 195.320 | 0.085 | sp$^3$C(+1) |
|  | 28 | 0.993 | 846.187 | 0.028 | O(−1) |
| Biphenyl Ureas | 132 | 0.913 | 265.566 | 0.106 | sp$^3$C(+1) |
| Aromatic Amides + ureas | 50 | 0.960 | 366.416 | 0.064 | O(−1) |

TABLE 2

Favorable and Unfavorable Positions for Substituents on Indoles

| Substituent | Favored position(s) | Unfavorable position(s) |
|---|---|---|
| Model 1: | | |
| —Cl(Ph at R$_1$) | | R$_5$ |
| —CH$_3$(Ph at R$_1$) | R$_2$ | R$_5$ |
| 2-naphthyl | R$_1$ | |
| anisole | R$_1$(ortho) | R$_1$(para) |
| t-butyl | | R$_1$ |
| Model 2: | | |
| —Cl | | R$_1$ |
| —CH$_3$ | R$_1$ | R$_2$ |
| —OMe | R$_2$ | R$_1$ |
| -Ph | Fused at R$_1$–R$_2$ | |
| Model 3: | | |
| (Ph at R$_1$) | | R$_4$ |
| -X(F or Cl), | | |
| —SO$_2$Me, | | |
| —CO$_2$H, | | |
| —CX$_3$ | | |

TABLE 2-continued

Favorable and Unfavorable Positions for Substituents on Indoles

| Substituent | Favored position(s) | Unfavorable position(s) |
|---|---|---|
| (Ph at $R_1$) | $R_4$ | |
| —$SO_3H$, | | |
| —$NH_2$ | | |
| (2-naphthyl at $R_1$) | $R_1$ | |
| —$CX_3$ | | |

Indole Models 1–3:

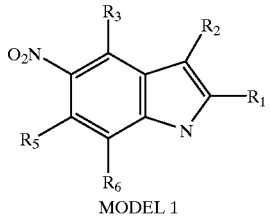

MODEL 1

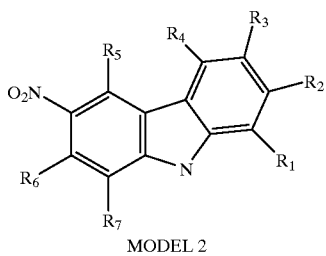

MODEL 2

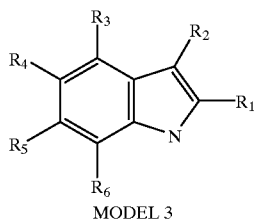

MODEL 3

Overall, using the models above, enhanced activity is suggested when more bulky groups are placed at $R_1$, and where the nitro group is on Models 1 and 2, or in the vicillity of $R_3$, $R_4$, and $R_5$ for the more general Model 3. It appears that it would be best if $R_2$ and $R_6$ were simply hydrogens. Electrostatically, the substituent(s) at the $R_3$, $R_4$, or $R_5$ position is optimal if it were a strong electron withdrawing group so as to result in a more negative region in these areas and a more positive region surrounding the indole ring center. There doesn't seem to be much preference for charge on the substituent at $R_1$, except for a few, very small areas where a negative charge may be favored.

From these results, 30 new indole compounds were analyzed using this model to predict their activity to see (1) if there is a better substituent at $R_1$ besides a phenyl group. and (2) if there is a more favorable substituent for the $R_4$ position in place of a nitro group. Table 2 summarizes the groups that had an extreme impact on increasing or decreasing the activity. In terms of $R_1$, 2-naphthyl and o-anisole, XII and VIII, were predicted to show comparable activity to INF55. Two others were predicted to be slightly less potent than INF55, having a naphthyl group fused to the indole rings, and the addition of a methyl group at the R. position along with the phenyl at the $R_1$, IX and XI. Therefore, the best group at $R_1$ would either be a phenyl or the 2-naphthyl. Using either the phenyl group or the 2-naphthyl at $R_1$, $R_4$ was then varied to find a more suitable group in place of the nitro. The sulfonyl group, shown in IV, is predicted to be the best of those looked at, not quite as active as the nitro group but it would still show at least a two-fold improvement over reserpine, known to be active at 5 µg/mL. Also of mention is placing an amine at the $R_4$ position, XIII which is predicted to be almost as active as the sulfonyl group. Other compounds that were predicted to be comparable to the activity of reserpine were the trifluoro- and trichloromethyl groups at $R_4$, and in these cases the 2-naphthyl group at $R_1$ as in XIV, showed better activity than the phenyl group.

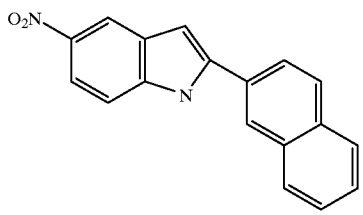

(XII)

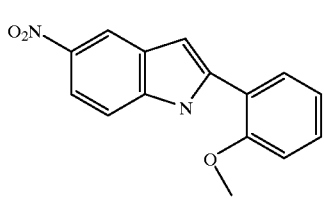

(VIII)

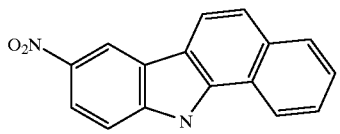

(IX)

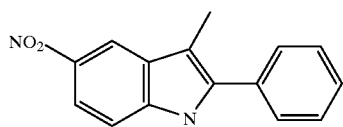

(XI)

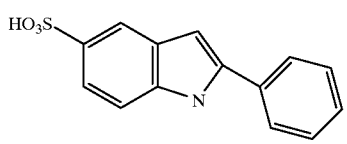

(IV)

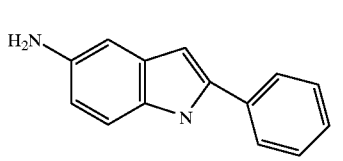

(XIII)

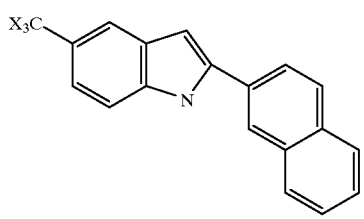

(XIV)

X = F or Cl

Overall for the indoles the CoMFA model suggests placing a more electronegative group at the $R_4$ position and an aromatic ring system at $R_1$. The aromatic ring system at $R_1$ would increase the size of the molecule, but at the same time keep the molecule relatively rigid and flat, an apparently favored 3D structure.

Ureas. Using original activity data along with activity data from newly synthesized biphenyl ureas, a new CoMFA model was generated. The best model for the urea system came from 132 compounds, using an sp³ carbon atom with a charge of +1, see Table 1. The steric field contour map with INF271, 276 placed within the field is shown if FIG. 3. Observation of the steric fields associated with the latest CoMFA model shows the following:

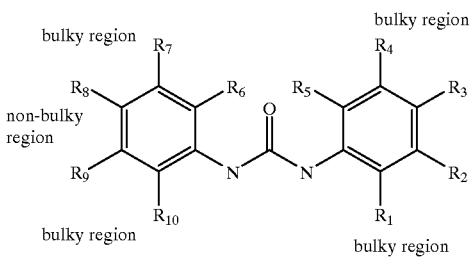

This new model reinforces the original one in that the bulkier substituents need to be placed away from the urea center. In addition it appears that the carbonyl group needs to remain "sterically unhindered", i.e. no substituenits at $R_5$ or $R_6$. The electrostatic field contour map is shown in FIG. 4. This updated electrostatic field suggests the following:

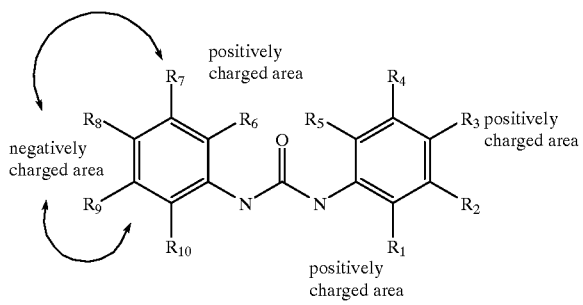

The electrostatic indications are that negatively charged groups, i.e. electron-withdrawing groups are favored in the region surrounding $R_7$, $R_8$, and $R_9$. Positively charged groups, those possessing very little electronegativity or being electron-donating groups are favored in the $R_1$ and $R_3$ positions. Positively charged groups are also favored in the $R_6$ and $R_7$ region as long as they are distanced fiom the aromatic ring. From the above results and based on the substituents known to enhance the activity of the biphellyl ureas, the following model is suggested.

Suggested Model for Ureas:

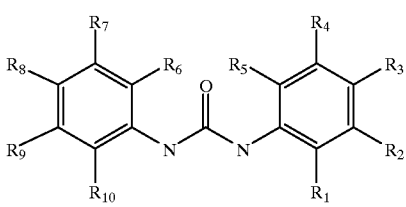

Favored: $R_1$ = ⁻OR; $R_3$ = alkyl; $R_4$ = ⁻Cl;
$R_7$–$R_8$ = Fused aromatic ring system or
$R_8$ = conjugated aromatic system;
$R_9$ = ⁻X (Br, Cl or F)

In this model, two positions are crucial, $R_1$ needs to have an alkoxy group and there needs to be an aromatic group at $R_8$ such as phelnyl, benzoyl, or a fused aromatic ring at $R_7$–$R_8$. There is also evidence that substituents can also be placed at $R_3$ and $R_9$. Currently the inventors plan to analyze yet more biphenyl ureas to further optimize these substituents for these positions.

Aromatic amides. Due to having the same pharmacaphore points within DISCO as the ureas, new CoMFA model and PLS analysis was performed using both aromatic amides and ureas. A total of 50 compounds were analyzed. The CoMFA results of the steric and electrostatic fields are in FIG. 5 and FIG. 6, placing INF240 within these contours. Using the model below, CoMFA suggests the following: bulky groups limited to $R_2$, and a long chain $R_6$ where the bulkier substituents are away from the aromatic amide itself. Also, if $R_6$ is not a long chain (less than 4 carbons) then substitution on the aromatic ring also can take place at the $R_4$ position. The $R_4$/$R_6$ combination must be fairly rigid and planar so as to keep the bulky groups in one region. Electrostatics once again indicates a large positive and large negative region on either side of the amide group(as in the urea system), and doesn't provide any indications away from this group.

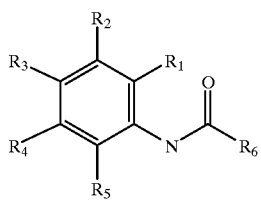

Summary

The CoMFA analysis has given suggestions for the indole systems, which have fairly rigid structures. From the original test-set, the sets of structurally diverse ureas and aromatic amide CoMFA's did not generate very specific models. However, upon further analysis, a large number of biphenyl ureas were found to have increased activity. From our compound set, 142 biphenyl ureas were found to be active (non-toxic and active at less than 10µg/ml). Of these 142 biphenyl ureas, 132 of them generated a reliable CoMFA analysis. The most recent CoMFA study for the ureas provides information regarding more optimal substituenits for enhancing the activity. The aromatic amides do not seem to be as promising of a lead model as either the indoles of ureas, most likely due to the much higher degree of flexibility of the compounds. However, limiting the type of aromatic amide, in much the same way as suggested for the ureas, may also be one alternative to better describing this system.

Example 2

Characterization of the Inhibitory Action of Identified Compounds

The present Example provides instructions regarding the measurement of the inhibitory activity of identified compounds.

Quantitation of Effects of Combination of Five Selected Inhibitors with Ethidium on Bacterial Growth.

Synergy testing was performed with the strain NA by checkerboard titration in microtiter plates using two-fold serial broth microdilution (Eliopoulus and Moellering Jr., 1996). Each candidate inhibitor was tested at 11 concentrations (ranging from 50 ng/ml –50 µg/ml) and ethidium was tested at 11 concentrations ranging from 30 ng/ml to 40

μg/ml (the MIC for the strain NA). Wells were assessed visually for growth after an 18 h incubation period. The Fractional Inhibitory Concentration (FIC) was calculated for each inhibitor and ethidium combination. The following formulae were used to calculate the FIC index:

$$\text{FIC of drug } A = \frac{\text{MIC of drug } A \text{ in combination}}{\text{MIC of drug } A \text{ alone}}$$

$$\text{FIC of drug } B = \frac{\text{MIC of drug } B \text{ in combination}}{\text{MIC of drug } B \text{ alone}}$$

FIC index = FIC of drug $A$ + FIC of drug $B$.

Synergy was defined as an FIC index of <0.5. FIG. 7 shows a representative synergy curve obtained for the combination of one of the inhibitors with ethidium. The calculated FIC indices are shown in Table 3.

TABLE 3

Synergy results for the combination of NorA inhibitors with ethidium.

| Inhibitor | FIC index |
| --- | --- |
| INF 55 | 0.08 |
| INF 240 | 0.16 |
| INF 271 | 0.07 |
| INF 277 | 0.09 |
| INF 392 | 0.14 |

The FIC indices for all five of the candidate inhibitors were <<0.5 indicating that these compounds were strongly synergistic in promoting the bacteriostatic effects of ethidium, which is what would be expected for an inhibitor of the ethiditim-resistanice mechanism, NorA in this particular case.

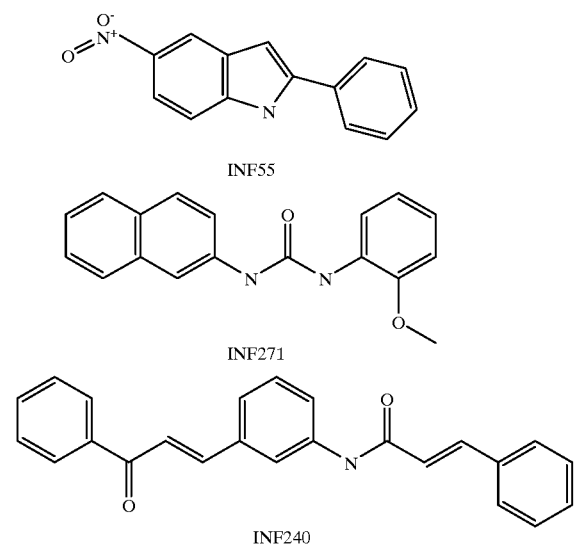

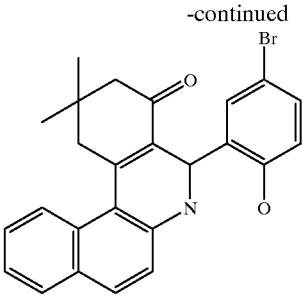

INF 277

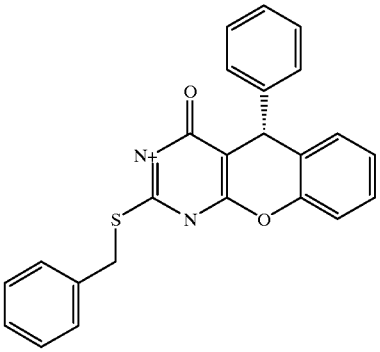

INF 392

Evaluation of Candidate Inhibitors Ability to Promote Toxicity by Suppressing Efflux by NorA.

NA cells over expressing NorA were loaded with ethidium bromide in the presence of reserpine (20 μg/ml). After washings cells were placed in a fluorimeter cuvette with fresh medium. Since ethidium fluoresces only when it is located inside the cell and bound to DNA, cells exhibited a rapid decrease in fluorescence due to NorA-mediated ethidium efflux. As shown in FIG. 8, this decrease in fluorescence was dramatically inhibited when cells were allowed to efflux in the presence of reserpine or each of the five tested compounds. The inventors conclude that the lead compounds synergistically promoted the toxicity of ethiditim bromide by inhibiting the efflux of the drug by the NorA multidrug efflux transporter.

Evaluation of Synergism Between Inhibitors and Ciprofloxacin in Promoting Bacteriotoxicity The inventors have quantitated the effects of the combination of the NorA inhibitors with ciprofloxacin, currently the most widely used fluoroquiniolone and the second most prescribed antibiotic. Synergy testing was performed by checkerboard titration as described above for ethidium. Eleven concentrations of ciprofloxacin ranging from 4 ng/ml to 4 μg/ml (two times the MIC) were used with both the NA strain and the *S. aureus* strain SA1199B which overexpresses NorA from a single chromosomal copy of the NorA gene (Kaatz et al., 1990). All five compounds acted in a synergistic manner with ciprofloxacin, having FIC indices <0.5 (see Table 4). The inventors concluded that, similarly to their effects on the bacteriotoxicity of ethidium, each of the tested NorA inhibitors promotes the bacteriotoxicity of ciprofloxacin in a synergistic manner.

TABLE 4

Synergy results for the combination of NorA inhibitors with ciprofloxacin.

| Inhibitor | INF 55 | INF 240 | INF 271 | INF 277 | INF 392 |
|---|---|---|---|---|---|
| FIC index NA | 0.25 | 0.12 | 0.12 | 0.15 | 0.28 |
| FIC index SA1199B | 0.25 | 0.28 | 0.18 | 0.28 | 0.15 |

Evaluate the Effect of the Inhibitors on the Intrinsic Susceptibility of Wild Type *S. aureus* to Ciprofloxacin.

The expression of NorA in wild type *S. aureus* confers significant intrinsic resistance to a number of fluoioquinolones including norfloxacin and ciprofloxacin (Yamada et al., 1997). The inventors therefore evaluated whether the newly identified inhibitors could potentiate the bacteriotoxic effects of fluoroquinolones in wild type *S. aureus*. As shown in FIG. 9 all of the identified NorA inhibitors decreased the $IC_{50}$ of ciprofloxacin by at least 3 fold. Thus the clinical use of any of the identified inhibitors in combination with ciprofloxacin would likely shift the $MIC_{90}$ of this antibiotic for *S. aureus* to well below the clinically achievable concentration. Since the frequency of emergence of low levet fluoroquinolone resistance can decrease by two orders of magnitude when selecting for a two-fold difference in the MIC (four times versus two times) (Wakabayashi and Mitsuhashi, 1994), the inventors next evaluated whether NorA inhibitors could, by promoting the intracellular accumulation of the antibiotic, decrease the rate of emergence of ciprofloxacin resistant variants.

Effect of Inhibitors on the Rate of Emergence of Ciprofloxacin Resistance in *S. aureus*.

The effect of the inhibitors on the rate of emergence of in vitro selected single-step ciprofloxacin resistant mutants of wild type *S. aureus* SA1199 (Kaatz et al., 1990) was determined. Spontaneous mutants were obtained 48 h after plating 2–4 33 $10^{10}$ SA1199 cells on LB agar plates containing ciprofloxacin at a concentration of 1 μg/ml (2×MIC). TFhe frequency of mutant selection was determined to be $2\times10^{-9}$ by comparing the number of colonies that grew on plates containing the drug with the number of colonies obtained upon plating appropriate dilutions in the absence of drug. Similar to the inventors' previous studies with norfiloxacin (Markham and Neyfakh, 1996), reserpine dramatically inhibited the emergence of ciprofloxacin resistance by more than one order of magnitude. Importantly, as shown in Table 5, each of the tested inhibitors also decreased the frequency of spontaneous emergence of ciprofloxacin resistance by 50-fold or more. This dramatic effect could not be attributed to a toxic effect of the inhibitor since the same concentration of inhibitor affected neither the colony forming ability, nor the colony size of SA1199 cells plated in the absence of ciprofloxacin.

TABLE 5

Frequency of emergence of in vitro selected variants of SA1199 resistant to two fold the MIC of ciprofloxacin in the absence or presence of NorA inhibitors.

| Inhibitor, concentration | Spontaneous | Mutagenized |
|---|---|---|
| None | $2.5 \times 10^{-9}$ | $2.5 \times 10^{-8}$ |
| Reserpine, 20 μg/ml | $<5 \times 10^{-11}$ | $<2.5 \times 10^{-10}$ |

TABLE 5-continued

Frequency of emergence of in vitro selected variants of SA1199 resistant to two fold the MIC of ciprofloxacin in the absence or presence of NorA inhibitors.

| Inhibitor, concentration | Spontaneous | Mutagenized |
|---|---|---|
| INF 55, 5 μg/ml | $<5 \times 10^{-11}$ | $<2.5 \times 10^{-10}$ |
| INF 240, 5 μg/ml | $<5 \times 10^{-11}$ | $<2.5 \times 10^{-10}$ |
| INF 271, 5 μg/ml | $<5 \times 10^{-11}$ | $<2.5 \times 10^{-10}$ |
| INF 277, 5 μg/ml | $<5 \times 10^{-11}$ | $<2.5 \times 10^{-10}$ |
| INF 392, 5 μg/ml | $<5 \times 10^{-11}$ | $1 \times 10^{-9}$ |

Ciprofloxacin resistance in first step in vitro selected mutants of *S. aureus* is predominantly due to specific point mutations in the targets of this drug, topoisomerase IV and gyrase (Cambau and Gutman, 1993, Ferrero et al., 1994). This explains why chemical mutagenesis of *S. aureus* by ethylmethane sulfonate increases the rate of emergence of ciprofloxacin-resistant variants by an order of magnitude (Table 5). However, even with mutagenized cells, the NorA inhibitors strongly suppressed the appearance of drug-resistant colonies. In conclusion, the identified lead inhibitors, like reserpine, inhibited the emergence of fluoroquinolone resistance in *S. aureus*.

Evaluate the Possibility of NorA Becoming Insensitive to the Inhibitors by Mutation.

One potential limitation to the combination of an antibiotic with an inhibitor of the resistance mechanism is the possibility of the resistance mechanism developing mutations making it insensitive to the inhibitor. Such a situation has been observed for bacteria which, through mutations in the β-lactamase gene, have developed resistance to Augmentin (a combination of ampicillin and clavulanic acid. an inhibitor of β-lactamase). Similarly, mutations in NorA could theoretically cause NorA to develop resistance to the inhibitor. Indeed, previous studies with Bmr, a close homolog of NorA, have shown that this multidrug efflux transporter can mutate to resist the inhibitory effects of reserpine while retaining drug eftiux activity (Ahmed et al., 1993).

To evaluate the possibility of such mutations arising in the NorA transporter the inventors determined the frequency of emergence of mutants of NorA-overexpressing *S. aureus*, SA1199B, that retained resistance to a NorA substrate in spite of the presence of a NorA inhibitor. These cells were chemically multageniized with ethiylmetlhanie sulfonate (Markham and Neyfakh, 1996) and $2-4\times10^9$ cells were then selected on plates containing the NorA substrate ethidium bromide (10 μg/ml—a quarter of the MIC) and either reserpine (20 μg/ml) or one or the five lead inhibitors (5 μg/ml). After a 48 h incubation period the number of colonies on each plate was determined.

Mutants insensitive to reserpine arose at a frequency of approximately $2\times10^{-8}$. As shown in Table 6, mutants insensitive to INF 392 arose at an even higher frequency. However, very few mutants ($2.5-5\times10^{-9}$) could be obtained with INF 277 and INF 240, and, most encouragingly, no mutants could be obtained which were insensitive to either INF 55 or INF 271. This strongly indicates the feasibility of developing an inhibitor to which NorA would be unable to adapt.

TABLE 6

Summary of the properties of the lead NorA inhibitors

| Inhibitor | INF 55 | INF 240 | INF 271 | INF 277 | INF 392 | Reserpine |
|---|---|---|---|---|---|---|
| Effectivity IC$_{50}$* S. Aureus, µg/ml | 1.5 | 0.8 | 1.5 | 0.8 | 0.1 | 6.25 |
| Toxicity HeLa IC$_{50}$, µg/ml | 40 | 2 | 18 | 5 | 45 | N.D |
| Selectivity Index (Toxicity HeLa/Effectivity) | 27 | 2.5 | 12 | 6 | 450 | N.D. |
| Fold inhibition of emergence of resistance | >50 | >50 | >50 | >50 | 25 | >50 |
| Frequency of adaptation of NorA | <5 × 10$^{-10}$ | <5 × 10$^{-9}$ | <5 × 10$^{-10}$ | <5 × 10$^{-9}$ | <5 × 10$^{-7}$ | <5 × 10$^{-8}$ |
| IC$_{50}$ S. Pneumoniae, µg/ml | 5 | N.A. | 2.5 | 5 | 2.5 | 5 |

*IC$_{50}$ for S. aureus (SA1199B) and S. pneumoniae (SPC2A) is defined here as the minimal concentration of drug required to decrease the MIC for ciprofloxacin by two fold. N.A. = not active at 5 µg/ml. N.D. = not determined.

Example 3

Toxicity Testing of Identified Inhibitors

Here the inventors proposed to test the toxicity of the identified lead compounds on several human cell lines. To date, the inventors have detemined the IC$_{50}$ of the lead compounds for the HeLa cell line, the results of which are presented in Table 6. The toxicity of the compounds at concentrations ranging from 0.7 µ/ml to 100 µg/ml was determined in a 96 well plate by adding the compounds to cells 24 h after seeding at a density of 10$^4$ per well. After incubation with the compounds for 3 days the effect on cell growth was determined using, the Cell Titer 96 AQ$_{ueous}$ MTS-based assay (Promega, Madison, Wis.).

Example 4

Pharmaceutical Compositions of the Present Invention

The MDT composition s of the present invention may be formulated as tablets or as solutions for injection as discussed in the pharmaceutical compositions section therein above. Trhe present section is intended to provide illustrative examples of MDT compositions for use in treating a subject with a bacterial or fungal infection. In treating bacterial infections, these MDT compositions may thus be provided to the subject in combination with a fluoroqlinolone. The fluoroquinolone may be provided in a separate composition, or where the biological chemistry allows, the fluoroquinolone may form part of the active ingredients of the MDT composition. In treating fungal infection, the MDT compositions may be provided to the subject in combination with an antiamycotic agent.

Compositions containing a dose of 100, 200, 300, 400 or 500 mg of an MDT inhibitor of the present invention are prepared as follows. The appropriately hydrated or dehydrated form of the MDT inhibitor forms the active ingredient of the composition. In the tablet formulation, an exemplary excipient core may comprise wheat starch, gelatin, talc, magnesium stearate sodium carboxymethylstarch, for a core and the coating comprising hydroxypropyl methylcellulose, ethyl cellulose, dibutyl sebacate, titanium oxide, talc, polyethylene glycol 600.

In addition to a composition comprising a single MDT inhibitor, it is contemplated that the active ingredients of the composition may be formulated to include two or more of the MDT inhibitors to provide a broader spectrum of activity.

Furthermore, it is contemplated that the therapeutic compositions of the present invention may comprise as an additional active ingredient, one or more fluoroquilnolone such as for example, pefloxacin, norfioxacin, ciprofloxacin, ofloxacin, sparfloxacin, grepafloxacin, Bay 12-8039, trovafloxacin, DU6859a, sarafloxacin, LB20304. lcvofloxacin, enoxacin, fleroxacin, lomefloxacin, temofloxacini, arnifloxacin, tosufloxacin, flumequinie, rufloxacin, clinafloxacin and the like.

In antimycotic applications, the therapeutic compositions of the present invention may comprise as an additional active ingredient, one or more anti-fungal agent such as amphotericin B., flucytosine, ketoconazole, miconazole, itraconazole, fluconazole, griseofluconazole, nystatin, haloprogin, loprox, natamycin, undecylenic acid and the like.

It is understood that the above formulations are provided by way of an example. one of skill in the art would be able to formulate a composition in which the inhibitors identified herein may be placed into any pharmaceutical carrier for the purposes of therapeutic delivery.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,448,962
U.S. Pat. No. 4,499,091
U.S. Pat. No. 4,668,784
U.S. Pat. No. 4,704.459
U.S. Pat. No. 4,795,751
U.S. Pat. No. 5.532,239
DE Patent Number 3,142,854
EP Number 206283

Acar and Goldstein, "Trends in bacterial resistance to floroquinolones," Clin. Infect. Dis., 24(1):67–73, 1997.

Ahmed et al., "Mutants of the Bacillus subtilis multidrug transporter Bmr with altered sensitivity to the antihypertensive alkaloid reserpine," J. Biol. Chem., 268:11086–11089, 1993.

Ahmed et al., "A protein that activates expression of a multidrug efflux transporter upon binding the transporter substrates," *J. Biol. Chem.*, 269:28506–28513, 1994.

Ahmed et al., "Two highly similar multidrug transporters of *Bacillus subtilis* whose expression is differentially regulated," *J. Bacteriol.*, 177:3904–3910, 1995.

Baranova and Neyfakh, "Apparent involvement of a multidrug transporter in the fluoroquinolone resistance of *Staphylococcus aureus*," *Antimicrob. Agents Chemother.*, 41:1396–1398, 1997.

Bolhuis et al., "The Lactococcal lmrP gene encodes a proton motive force-dependent drug transporter." *J. Biol Chem.* 270(44): 26092–26098, 1995.

Brenwald et al., "The effect of reserpine, an inhibitor of multidrug efflux pumps, on the in vitro susceptibilities of fluorquinolone-resistant strains of *Streptococcus pneumoniae* to norfloxadiins," *Antimicriob. Agents Chemother.*, 40:458–460, 1997.

Brown, "The pyrimidines," Wiley Interscience, NY. pp 1–1 509. 1994.

Cambau and Gutman, "Mechanisms of resistance to quinolones," *Drugs*, 45:15–23, 1993.

Cormican and Jones, "Emerging resistance to antimicrobial agents in gram positive bacteria," *Drugs*, 51(1):6–12 1996.

Davis et al., "Ciprofloxacin," *Drugs*, 51(6): 1019–1074, 1996.

Dewar et al., *Am. Chem. Soc.*, 107:3902–3909, 1985.

Eliopoulus and Moellering, Antimicrobial combinations, In: *Antibiotics in laboratory medicine*, (ed.) Lorian, The Williams and Wilkins Co., Baltimore, Md., pp. 330–396, 1996.

Ferrero et al., "Cloning, and primary structure of *Staphylococcus aureus* DNA topoisomerase IV: a primary target of fluoroquinolones," *Mol. Microbiol.*, 13:641–653, 1994.

Jurczak and Golebiowski, "Optically Active N-protected amino Aldehydes in Organice Synthesis" *Chem. Rev.* 89, 149–164, 1989.

Kaatz and Seo, "Inducible NorA-mediated multidrug resistance in *Staphylococcus aureus* ," *Antimicrob. Agents Chemother.*, 39:2650–2655, 1995.

Kaatz, et al., "Mechanisms of fluoroquinolone resistance in *Staphylococcus aureus*," *J. Infect. Dis.*, 163:1080–1086, 1990.

Katritzky and Wang, 25:671–675, 1998.

Korten et al., "Analysis by PCR and direct sequencing of gyrA mutations associated with fluoroquinolone resistance in *Enterococcus faecalis*," *Antimicrob. Agents Chemother.*, 38:2091–2094, 1994.

Kulagowski et al., "Preparation and Rearrangement of 6a-Methyl-6aH-benzo[a]carbazole and 11b-Methyl-11bHbenzo[c]carbazole," *J. Chem. Soc. Perkin Trans.*, 1:2733–2739, 1985.

Lewis, "Multidrug-resistance pumps in bacteria: variations on a them," *Trends Biochem. Sci.*, 19:119–123, 1994.

Lomovskaya and Lewis, "Emr, and *E. coli* locus for multidrug resistance," *Proc. Natl. Acad. Sci. USA*, 89:8938–8942, 1992.

Lynch et al., "Active efflux of antimicrobial agents in wild-type strains of Enterococci," *Antimicrob. Agents Chemother.*, 41:869–87 1997.

Markham and Neyfakhi, "Inhibition of the multidrug transporter NorA prevents emergence of norfloxacin resistance in *Staphylococcus aureus*," *Antimicrob. Agents Chemother.*, 40:2673–2674, 1996.

Martin et al., "A fast new approach to pharmacophore mapping, and its application to dopaminergic and benzodiazepine agonists" *J. Computer-Aided Molec. Design*, 7:83–102, 1993.

Maryanoff and Reitz "The Wittig Olefination Reaction and modifications involving Phosphoryl-stablizied carbanions. Stereochemistry, mechanism and selected synthetic aspects", *Chem. Rev.* 89, 863–927, 1989.

Munoz and De La Campa, "ParC subunit of DNA topoisomerase IV of *Streptococcus pneumoniae* is a primary target of fluoroquinolones and cooperates with DNA gyrase A subunit in forming resistance phenotype," *Antimicrob. Agents Chemother.*, 40:2252–2257, 1996.

Neyfakh, "The multidrug efflux transporter of *Bacillus subtilis* is a structural and functional homolog of the Staphlococcus NorA protein," *Antimicrob. Agents Chemother.*, 36:484–485, 1992.

Neyfakh et al., "Efflux-mediated multidrug resistance in *Bacillus subtilis*: similarities and dissimilarities with the mammalian system," *Proc. Natl. Acad. Sci. USA*, 88:4781–4785.

Neyfakh et al., "Fluoroquinolone resistance protein NorA of *Staphylococcus aureus* is a multidrug efflux transporter," *Antimicrob. Agents Chemother.*, 37:128–129, 1993.

Nikaido, "Prevention of drug access to bacteria targets: permeability barriers and active efflux," *Science*, 264:382–388, 1994.

Novick, "The Staphylococcus as a molecular genetic system," In: *Molecular biology of the Staphylococci*, (ed) Novick, VCH Publishers, N.Y., p. 1–37, 1990.

Ohki and Murata, "bmr3, a third multidrug transporter gene of *Bacillus subtilis*," *J. Bacteriol.*, 179:1423–1427, 1997.

Okusu et al., "AcrAB efflux pump plays a major role in the antibiotic resistance phenotype of *E. coli* multiple-antibiotic-resistance (Mar) mutants," *J. Bacteriol.*, 178:306–308, 1996.

Poole et al., "Multiple antibiotic resistance in *Pseudomonas aeruginosa*: evidence for involvement of an efflux operon," *J. Bacteriol.*, 175:7363–7372, 1993.

Robinson, "The Fischer Indole synthesis," Wiley, Chichester, pp. 1–923, 1982.

Staab and Benz, *Liebigs Ann.*, (72)648, 1961.

Stein, "Kinetics of the multidrug transporter (P-glycoprotein) and its reversal," *Physiol. Rev.*, 77:545–589, 1997.

Takiff et al., "Efflux pumps of the proton antiporter family confer low level fluoroquinolone resistance in *Mycobacterium smegamatis*," *Proc. Natl. Acad. Sci. USA*, 93:362–366, 1996.

Tankovic et al., "Contribution of mutations in gyrA and parC genes to fluoroquinolone resistance of mutants of *Streptococcus pneumoniae* obtained in vivo and in vitro," *Antimicrob. Agents Chemother.*, 40:2505–2510, 1996.

Trucksis et al., "A novel locus conferring fluoroquinolone resistance in *Straphylococcus aureus*," *J. Bacteriol.*, 1773:5854–5860,1991.

U.S. Food and Drug Administration, "New antimicrobial agents approved in 1996 and new indications for previously used agents," *Antimicrob. Agents Chemother.*, 41:878, 1997.

van Veen et al., "Multidrug resistance mediated by a bacterial homolog of the human multidrug transporter MDR1." *Proc Natl Acad Sci USA*. 93(20): 10668–10672, 1996.

Vedejs and Peterson, "Stereochemistry and Mechanism in the Wittig Reaction", *Top. Stereochem.*, 21, 1–157, 1994.

Wakabayashi and Mitsuhashi, "In vitro antibacterial activity of AM-1155, a new 6-fluoro-8-methoxy quinoloine," *Antimicrob. Agents Chemother.*, 38:594–601, 1994.

Yamada et al., "Quinolone susceptibility of norA-disrupted *Staphylococcus aureus*," *Antimicrob. Agents Chemother.*, 41:2308–2309, 1997.

Yoshida et al., "Nucleotide sequence and characterization of the *Staphylococcus aureus* nor A gene, which confers resistance to quinolones," *J. Bacteriol.*, 172:6942–6949, 1990.

Zeller et al., "Active efflux as a mechanism of resistance to ciprofloxacin in *Streptococcus pneumoniae*," *Antimicrob. Agent Chemother.*, 41:1973–1978, 1997.

Zhou et al., "Multiple binding modes of flavones as protein tyrosine kinase inhibitors," *J. Computer-Aided Molec. Design,*.

What is claimed is:

1. A method for enhancing the antibacterial action of fluorquinolones comprising contacting a bacterium with an indole inhibitor of NorA, said indole having the formula:

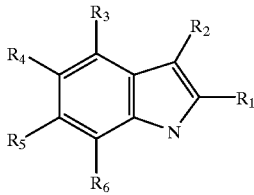

(I)

wherein $R_1$ is phenyl, 2-napthyl, o-anisole, $R_2$ is H or $CH_3$, $R_1$ and $R_2$ are two napthyl groups fused to the indole ring, $R_3$ is H, $R_4$ is $NO_2$, $SO_3H$, $NH_2$, $CF_3$ or $CCl_3$, $R_5$ is H, and $R_6$ is H.

2. The method of claim 1, wherein $R_1$ is phenyl and $R_4$ is $SO_3H$ or $NO_2$.

3. The method of claim 1, wherein $R_1$ is 2-naphthyl and $R_4$ is $CCl_3$ or $CF_3$.

4. The method of claim 1, wherein $R_1$ is o-anisole and $R_4$ is $NO_2$.

5. The method of claim 1, wherein $R_1$ and $R_2$ are two naphthyl groups fused to the indole ring.

6. The method of claim 1, wherein $R_1$ is phenyl and $R_2$ is $CH_3$.

7. The method of claim 1, wherein said bacterium is *Streptococcus pneumonia, Enterococcus faecalis, Staphylococcus aureus, Streptococcus pygenes, Escherichia coli, Psuedomonas aeruginosa, Staphylococcus epidermis, Mycobacterium tuberculosis, Mycobacterium smegmatis* and *Serratia marcesens*.

8. An indole having the formula:

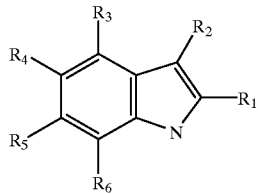

(I)

wherein $R_1$ is phenyl, 2-napthyl, o-anisole, $R_2$ is H or $CH_3$, $R_1$ and $R_2$ are two napthyl groups fused to the indole ring, $R_3$ is H, $R_4$ is $NO_2$, $SO_3H$, $NH_2$, $CF_3$ or $CCl_3$, $R_5$ is H, and $R_6$ is H.

9. The indole of claim 8, wherein $R_1$ is phenyl and $R_4$ is $SO_3H$ or $NO_2$.

10. The indole of claim 8, wherein $R_1$ is 2-naphthyl and $R_4$ is $CCl_3$ or $CF_3$.

11. The indole of claim 8, wherein $R_1$ is o-anisole and $R_4$ is $NO_2$.

12. The indole of claim 8, wherein $R_1$ and $R_2$ are two naphthyl groups fused to the indole ring.

13. The indole of claim 8, wherein $R_1$ is phenyl and $R_2$ is $CH_3$.

14. A pharmaceutical composition comprising a fluoroquinolone and an indole inhibitor of NorA, said indole having the formula:

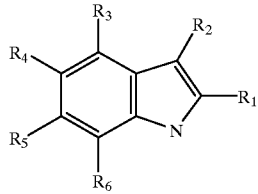

(I)

wherein $R_1$ is phenyl, 2-napthyl, o-anisole, $R_2$ is H or $CH_3$, $R_1$ and $R_2$ are two napthyl groups fused to the indole ring, $R_3$ is H, $R_4$ is $NO_2$, $SO_3H$, $NH_2$, $CF_3$ or $CCl_3$, $R_5$ is H, and $R_6$ is H.

* * * * *

UNITED STATES PATENT AND TRADEMARK OFFICE
CERTIFICATE OF CORRECTION

PATENT NO. : 6,326,391 B1
DATED : December 4, 2001
INVENTOR(S) : Penelope N. Markhamm, Debbie C. Mulheam, Alexander A. Neyfakh, David Crich, Mohamad-Rami Jaber and Michael E. Johnson It is certified that error appears in the above-identified patent and that said Letters Patent is hereby corrected as shown below:

Column 55,
Line 28, please delete "2-napthyl" and insert -- 2-naphthyl -- therefor.
Line 29, please delete the word "napthyl" and insert the word -- naphthyl -- therefor.
Line 44, please delete the words "*Streptococcus pygenes*" and insert the words
-- *Streptococcus pyogenes* -- therefor.

Column 56,
Line 13, please delete "$_2$-napthyl" and insert -- 2-naphthyl -- therefor.

Signed and Sealed this

Third Day of September, 2002

*Attest:*

JAMES E. ROGAN
*Attesting Officer*  *Director of the United States Patent and Trademark Office*